US009127249B2

(12) United States Patent
Yun et al.

(10) Patent No.: US 9,127,249 B2
(45) Date of Patent: Sep. 8, 2015

(54) METHOD FOR PREPARING METABOLITES OF ATORVASTATIN USING BACTERIAL CYTOCHROME P450 AND COMPOSITION THEREFOR

(71) Applicant: INDUSTRY FOUNDATION OF CHONNAM NATIONAL UNIVERSITY, Gwangju (KR)

(72) Inventors: Chul-Ho Yun, Daejeon (KR); Dong-Hyun Kim, Gongju-si (KR); Ji-Yeon Kang, Daejeon (KR); Sun-Ha Park, Gwangju (KR); Sang-Hoon Ryu, Gwangju (KR)

(73) Assignee: INDUSTRY FOUNDATION OF CHONNAM NATIONAL UNIVERSITY (KR)

( * ) Notice: Subject to any disclaimer, the term of this patent is extended or adjusted under 35 U.S.C. 154(b) by 0 days.

(21) Appl. No.: 13/639,589

(22) PCT Filed: Sep. 27, 2012

(86) PCT No.: PCT/KR2012/007779

§ 371 (c)(1), (2) Date: Oct. 5, 2012

(87) PCT Pub. No.: WO2013/073775

PCT Pub. Date: May 23, 2013

(65) Prior Publication Data

US 2014/0308716 A1 Oct. 16, 2014

(30) Foreign Application Priority Data

Nov. 15, 2011 (KR) ........................ 10-2011-0118814
Aug. 29, 2012 (KR) ........................ 10-2012-0094935

(51) Int. Cl.
*C12P 17/10* (2006.01)
*C12N 9/02* (2006.01)

(52) U.S. Cl.
CPC ............... *C12N 9/0071* (2013.01); *C12P 17/10* (2013.01); *C12Y 114/14001* (2013.01)

(58) Field of Classification Search
CPC ............................ C12N 9/0071; C12N 9/0073
See application file for complete search history.

(56) References Cited

U.S. PATENT DOCUMENTS 7,531,335 B1 * 5/2009 Hauer et al. .................. 435/189
7,981,652 B2 * 7/2011 Hauer et al. .................. 435/189

(Continued)

FOREIGN PATENT DOCUMENTS

WO 2011025203 3/2011

OTHER PUBLICATIONS

T. H. Rushmore, et al., Bioreactor Systems in Drug Metabolism: Synthesis of Cytochrome P450-Generated Metabolites, Metabolic Engineering 2, 2000, pp. 115-125.

(Continued)

*Primary Examiner* — Manjunath Rao
*Assistant Examiner* — William W Moore
(74) *Attorney, Agent, or Firm* — Cantor Colburn LLP

(57) ABSTRACT

Provided is a novel method for preparing metabolites of atorvastatin using bacterial cytochrome P450, and a composition therefor, and more particularly, a composition for preparing 2-hydroxylated product of 4-hydroxylated product from atorvastatin including bacterial cytochrome P 450 BM3 (CYP102A1), CYP102A1 mutants, and chimeras derived from the CYP102A1 mutants, a kit therefor, and a method for preparing thereof.

3 Claims, 14 Drawing Sheets

(56) References Cited

U.S. PATENT DOCUMENTS

| | | | | |
|---|---|---|---|---|
| 8,026,085 | B2 * | 9/2011 | Fasan et al. | 435/132 |
| 8,252,559 | B2 * | 8/2012 | Fasan et al. | 435/132 |
| 8,603,949 | B2 * | 12/2013 | Arnold et al. | 506/24 |
| 8,802,401 | B2 * | 8/2014 | Arnold et al. | 435/132 |
| 2005/0059045 | A1 * | 3/2005 | Arnold et al. | 435/6 |
| 2008/0248545 | A1 * | 10/2008 | Arnold et al. | 435/183 |
| 2008/0268517 | A1 * | 10/2008 | Arnold et al. | 435/189 |
| 2009/0124515 | A1 * | 5/2009 | Arnold et al. | 506/11 |
| 2010/0217032 | A1 * | 8/2010 | Klaassen et al. | 560/194 |
| 2010/0240106 | A1 * | 9/2010 | Wong et al. | 435/134 |
| 2010/0267083 | A1 * | 10/2010 | Hauer et al. | 435/69.1 |
| 2011/0236940 | A1 * | 9/2011 | Yun et al. | 435/156 |
| 2012/0171693 | A1 * | 7/2012 | Arnold et al. | 435/6.18 |
| 2012/0202256 | A1 * | 8/2012 | Yun et al. | 435/125 |
| 2014/0038850 | A1 * | 2/2014 | Fasan et al. | 506/11 |

OTHER PUBLICATIONS

C. H. Yun, et al., Functional Expression of Human Cytochrome P450 Enzymes in *Escherichia coli*, Current Drug Metabolism, 2006, pp. 411-429.

C. R. Otey, et al., Preparation of Human Metabolites of Propranolol Using Laboratory-Evolved Bacterial Cytochromes P450, Wiley Periodicals, 2005, pp. 494-499.

D. H. Kim, et al., Heterologous expression and characterization of wild-type human cytochrome P450 1A2 without conventional N-terminal modification in *Escherichia coli*, Protein Expression and Purification 57, 2008, pp. 188-200.

C. H. Yun, et al., The bacterial P450 BM3: a prototype for a biocatalyst with human P450 activities, Trends in Biotechnology, vol. 25, pp. 289-298, 2007.

G. Di Nardo, et al, Wild-type CYP102A1 as a biocatalyst: turnover of drugs usually metabolised by human liver enzymes, J Biol Inorg Chem 2007, pp. 313-323.

Kim, et al., Generation of Human Metabolites of 7-Ethoxycoumarin by Bacterial Cytochrome P450 BM3, Drug Metabolism and Disposition, 2008, pp. 2166-2170.

Prueksaritanont, et al., Glucuronidation of Statins in Animals and Humans: A Novel Mechanism of Statin Lactonization, Drug Metabolism and Disposition, 2002, pp. 505-512.

W. Jacobsen et al., Lactonization Is the Critical First Step in the Disposition of the 3-Hydroxy-3-Methylglutaryl-CoA Reductase Inhibitor Atorvastatin, Drug Metabolism and Disposition, 2000, pp. 1369-1378.

E. Vottero et al., Role of residue 87 in substrate selectivity and regioselectivity of drug-metabolizing cytochrome P450 CYP102A1 M11, J Biol Inorg Chem, 2011, pp. 899-912.

* cited by examiner

Fig. 1

| | |
|---|---|
| 1 | MTIKEMPQPKTFGELKNLPLLNTDKPVQALMKIADELGEIFKFEAPGRVTRYLSSQRLIK |
| 61 | EACDESRFDKNLSQALKFVRDFAGDGLFTSWTHEKNWKKAHNILLPSFSQQAMKGYHAMM |
| 121 | VDIAVQLVQKWERLNADEHIEVPEDMTRLTLDTIGLCGFNYRFNSFYRDQPHPFITSMVR |
| 181 | ALDEAMNKLQRANPDDPAYDENKRQFQEDIKVMNDLVDKIIADRKASGEQSDDLLTHMLN |
| 241 | GKDPETGEPLDDENIRYQIITFLIAGHETTSGLLSFALYFLVKNPHVLQKAAEEAARVLV |
| 301 | DPVPSYKQVKQLKYVGMVLNEALRLWPTAPAFSLYAKEDTVLGGEYPLEKGDELMVLIPQ |
| 361 | LHRDKTIWGDDVEEFRPERFENPSAIPQHAFKPFGNGQRACIGQQFALHEATLVLGMMLK |
| 421 | HFDFEDHTNYELDIKETLTLKPEGFVVKAKSKKIPLGGIPSPSTEQSAKKVRKKAENAHN |
| 481 | TPLLVLYGSNMGTAEGTARDLADIAMSKGFAPQVATLDSHAGNLPREGAVLIVTASYNGH |
| 541 | PPDNAKQFVDWLDQASADEVKGVRYSVFGCGDKNWATTYQKVPAFIDETLAAKGAENIAD |
| 601 | RGEADASDDFEGTYEEWREHMWSDVAAYFNLDIENSEDNKSTLSLQFVDSAADMPLAKMH |
| 661 | GAFSTNVVASKELQQPGSARSTRHLEIELPKEASYQEGDHLGVIPRNYEGIVNRVTARFG |
| 721 | LDASQQIRLEAEEEKLAHLPLAKTVSVEELLQYVELQDPVTRTQLRAMAAKTVCPPHKVE |
| 781 | LEALLEKQAYKEQVLAKRLTMLELLEKYPACEMKFSEFIALLPSIRPRYYSISSSPRVDE |
| 841 | KQASITVSVVSGEAWSGYGEYKGIASNYLAELQEGDTITCFISTPQSEFTLPKDPETPLI |
| 901 | MVGPGTGVAPFRGFVQARKQLKEQGQSLGEAHLYFGCRSPHEDYLYQEELENAQSEGIIT |
| 961 | LHTAFSRMPNQPKTYVQHVMEQDGKKLIELLDQGAHFYICGDGSQMAPAVEATLMKSYAD |
| 1021 | VHQVSEADARLWLQQLEEKGRYAKDVWAG- |

※ An amino acid sequence of mutants produced by site-directed mutation of wild-type CYP102A1 starts from threonine (T), which is a second amino acid, rather than methionine (M).

Fig. 2

```
5' -ATGACAATTAAAGAAATGCCTCAGCCAAAAACGTTTGGAGAGCTTAAAAATTTACCGTTATTA
AACACAGATAAACCGGTTCAAGCTTTGATGAAAATTGCGGATGAATTAGGAGAAATCTTTAAA
TTCGAGGCGCCTGGTCGTGTAACGCGCTACTTATCAAGTCAGCGTCTAATTAAAGAAGCATGC
GATGAATCACGCTTTGATAAAAACTTAAGTCAAGCGCTTAAATTTGTACGTGATTTTGCAGGA
GACGGGTTATTTACAAGCTGGACGCATGAAAAAAATTGGAAAAAGCGCATAATATCTTACTT
CCAAGCTTCAGTCAGCAGGCAATGAAAGGCTATCATGCGATGATGGTCGATATCGCCGTGCAG
CTTGTTCAAAAGTGGGAGCGTCTAAATGCAGATGAGCATATTGAAGTACCGGAAGACATGACA
CGTTTAACGCTTGATACAATTGGTCTTTGCGGCTTTAACTATCGCTTTAACAGCTTTTACCGA
GATCAGCCTCATCCATTTATTACAAGTATGGTCCGTGCACTGGATGAAGCAATGAACAAGCTG
CAGCGAGCAAATCCAGACGACCCAGCTTATGATGAAAACAAGCGCCAGTTTCAAGAAGATATC
AAGGTGATGAACGACCTAGTAGATAAAATTATTGCAGATCGCAAAGCAAGCGGTGAACAAAGC
GATGATTTATTAACGCATATGCTAAACGGAAAAGATCCAGAAACGGGTGAGCCGCTTGATGAC
GAGAACATTCGCTATCAAATTATTACATTCTTAATTGCGGGACACGAAACAACAAGTGGTCTT
TTATCATTTGCGCTGTATTTCTTAGTGAAAAATCCACATGTATTACAAAAAGCAGCAGAAGAA
GCAGCACGAGTTCTAGTAGATCCTGTTCCAAGCTACAAACAAGTCAAACAGCTTAAATATGTC
GGCATGGTCTTAAACGAAGCGCTGCGCTTATGGCCAACTGCTCCTGCGTTTTCCCTATATGCA
AAAGAAGATACGGTGCTTGGAGGAGAATATCCTTTAGAAAAAGGCGACGAACTAATGGTTCTG
ATTCCTCAGCTTCACCGTGATAAAACAATTTGGGGAGACGATGTGGAAGAGTTCCGTCCAGAG
CGTTTTGAAAATCCAAGTGCGATTCCGCAGCATGCGTTTAAACCGTTTGGAAACGGTCAGCGT
GCGTGTATCGGTCAGCAGTTCGCTCTTCATGAAGCAACGCTGGTACTTGGTATGATGCTAAAA
CACTTTGACTTTGAAGATCATACAAACTACGAGCTCGATATTAAAGAAACTTTAACGTTAAAA
CCTGAAGGCTTTGTGGTAAAAGCAAAATCGAAAAAAATTCCGCTTGGCGGTATTCCTTCACCT
AGCACTGAACAGTCTGCTAAAAAAGTACGCAAAAAGGCAGAAAACGCTCATAATACGCCGCTG
CTTGTGCTATACGGTTCAAATATGGGAACAGCTGAAGGAACGGCGCGTGATTTAGCAGATATT
GCAATGAGCAAAGGATTTGCACCGCAGGTCGCAACGCTTGATTCACACGCCGGAAATCTTCCG
CGCGAAGGAGCTGTATTAATTGTAACGGCGTCTTATAACGGTCATCCGCCTGATAACGCAAAG
CAATTTGTCGACTGGTTAGACCAAGCGTCTGCTGATGAAGTAAAAGGCGTTCGCTACTCCGTA
TTTGGATGCGGCGATAAAAACTGGGCTACTACGTATCAAAAAGTGCCTGCTTTTATCGATGAA
ACGCTTGCCGCTAAAGGGGCAGAAAACATCGCTGACCGCGGTGAAGCAGATGCAAGCGACGAC
TTTGAAGGCACATATGAAGAATGGCGTGAACATATGTGGAGTGACGTAGCAGCCTACTTTAAC
CTCGACATTGAAAACAGTGAAGATAATAAATCTACTCTTTCACTTCAATTTGTCGACAGCGCC
GCGGATATGCCGCTTGCGAAAATGCACGGTGCGTTTTCAACGAACGTCGTAGCAAGCAAAGAA
CTTCAACAGCCAGGCAGTGCACGAAGCACGCGACATCTTGAAATTGAACTTCCAAAAGAAGCT
TCTTATCAAGAAGGAGATCATTTAGGTGTTATTCCTCGCAACTATGAAGGAATAGTAAACCGT
GTAACAGCAAGGTTCGGCCTAGATGCATCACAGCAAATCCGTCTGGAAGCAGAAGAAGAAAAA
TTAGCTCATTTGCCACTCGCTAAAACAGTATCCGTAGAAGAGCTTCTGCAATACGTGGAGCTT
CAAGATCCTGTTACGCGCACGCAGCTTCGCGCAATGGCTGCTAAAACGGTCTGCCCGCCGCAT
AAAGTAGAGCTTGAAGCCTTGCTTGAAAAGCAAGCCTACAAAGAACAAGTGCTGGCAAAACGT
TTAACAATGCTTGAACTGCTTGAAAAATACCCGGCGTGTGAAATGAAATTCAGCGAATTTATC
GCCCTTCTGCCAAGCATACGCCCGCGCTATTACTCGATTTCTTCATCACCTCGTGTCGATGAA
AAACAAGCAAGCATCACGGTCAGCGTTGTCTCAGGAGAAGCGTGGAGCGGATATGGAGAATAT
AAAGGAATTGCGTCGAACTATCTTGCCGAGCTGCAAGAAGGAGATACGATTACGTGCTTTATT
TCCACACCGCAGTCAGAATTTACGCTGCCAAAAGACCCTGAAACGCCGCTTATCATGGTCGGA
CCGGGAACAGGCGTCGCGCCGTTTAGAGGCTTTGTGCAGGCGCGCAAACAGCTAAAAGAACAA
GGACAGTCACTTGGAGAAGCACATTTATACTTCGGCTGCCGTTCACCTCATGAAGACTATCTG
TATCAAGAAGAGCTTGAAAACGCCCAAAGCGAAGGCATCATTACGCTTCATACCGCTTTTTCT
CGCATGCCAAATCAGCCGAAAACATACGTTCAGCACGTAATGGAACAAGACGGCAAGAAATTG
ATTGAACTTCTTGATCAAGGAGCGCACTTCTATATTTGCGGAGACGGAAGCCAAATGGCACCT
GCCGTTGAAGCAACGCTTATGAAAAGCTATGCTGACGTTCACCAAGTGAGTGAAGCAGACGCT
CGCTTATGGCTGCAGCAGCTAGAAGAAAAAGGCCGATACGCAAAAGACGTGTGGGCTGGGTAA-3'
```

Fig. 3

Amino acid sequence of wild-type CYP102A1 mutant #16 (M16)

| | |
|---|---|
| 1 | MTIKEMPQPKTFGELKNLPLLNTDKPVQALMKIADELGEIFKFEAPGRVTRYLSSQRLIK |
| 61 | EACDESRFDKNLSQALKFVRDFAGDGLFTSWTHEKNWKKAHNILLPSFSQQAMKGYHAMM |
| 121 | VDIAVQLVQKWERLNADEHIEVPEDMTRLTLDTIGLCGFNYRFNSFYRDQPHPFITSMVR |
| 181 | ALDEAMNKLQRANPDDPAYDENKRQFQEDIKVMNDLVDKIIADRKASGEQSDDLLTHMLN |
| 241 | GKDPETGEPLDDENIRYQIITFLIAGHETTSGLLSFALYFLVKNPHVLQKAAEEAARVLV |
| 301 | DPVPSYKQVKQLKYVGMVLNEALRLWPTAPAFSLYAKEDTVLGGEYPLEKGDELMVLIPQ |
| 361 | LHRDKTIWGDDVEEFRPERFENPSAIPQHAFKPFGNGQRACIGQQFALHEATLVLGMMLK |
| 421 | HFDFEDHTNYELDIKETLTLKPEGFVVKAKSKKIPLGGIPSPSTEQSAKKVRKKAENAHN |
| 481 | TPLLVLYGSNMGTAEGTARDLADIAMSKGFAPQVATLDSHAGNLPREGAVLIVTASYNGH |
| 541 | PPDNAKQFVDWLDQASADEVKGVRYSVFGCGDKNWATTYQKVPAFIDETLAAKGAENIAD |
| 601 | RGEADASDDFEGTYEEWREHMWSDVAAYFNLDIENSEDNKSTLSLQFVDSAADMPLAKMH |
| 661 | GAFSTNVVASKELQQPGSARSTRHLEIELPKEASYQEGDHLGVIPRNYEGIVNRVTARFG |
| 721 | LDASQQIRLEAEEEKLAHLPLAKTVSVEELLQYVELQDPVTRTQLRAMAAKTVCPPHKVE |
| 781 | LEALLEKQAYKEQVLAKRLTMLELLEKYPACEMKFSEFIALLPSIRPRYYSISSSPRVDE |
| 841 | KQASITVSVVSGEAWSGYGEYKGIASNYLAELQEGDTITCFISTPQSEFTLPKDPETPLI |
| 901 | MVGPGTGVAPFRGFVQARKQLKEQGQSLGEAHLYFGCRSPHEDYLYQEELENAQSEGIIT |
| 961 | LHTAFSRMPNQPKTYVQHVMEQDGKKLIELLDQGAHFYICGDGSQMAPAVEATLMKSYAD |
| 1021 | VHQVSEADARLWLQQLEEKGRYAKDVWAG- |

Fig. 4

5′ -ATGACAATTAAAGAAATGCCTCAGCCAAAAACGTTTGGAGAGCTTAAAAATTTaCCGTTATTA
AACACAGATAAACCGGTTCAAGCTTTGATGAAAATTGCGGATGAATTAGGAGAAATCTTTAAA
TTCGAGGCGCCTGGTCTTGTAACGCGCTACTTATCAAGTCAGCGTCTAATTAAAGAAGCATGC
GATGAATCACGCTTTGATAAAAACTTAAGTCAAGCGCTTAAATTTGTACGTGATATTGCAGGA
GACGGGTTAGTTACAAGCTGGACGCATGAAAAAAATTGGAAAAAGCGCATAATATCTTACTT
CCAAGCTTCAGTCAGCAGGCAATGAAAGGCTATCATGCGATGATGGTCGATATCGCCGTGCAG
CTTGTTCAAAAGTGGGAGCGTCTAAATGCAGATGAGCATATTGAAGTACCGGGAGACATGACA
CGTTTAACGCTTGATACAATTGGTCTTTGCGGCTTTAACTATCGCTTTAACAGCTTTTACCGA
GATCAGCCTCATCCATTTATTACAAGTATGGTCCGTGCACTGGATGAAGCAATGAACAAGCAG
CAGCGAGCAAATCCAGACGACCCAGCTTATGATGAAAACAAGCGCCAGTTTCAAGAAGATATC
AAGGTGATGAACGACCTAGTAGATAAAATTATTGCAGATCGCAAAGCAAGCGGTGAACAAAGC
GATGATTTATTAACGCATATGCTAAACGGAAAAGATCCAGAAACGGGTGAGCCGCTTGATGAC
GAGAACATTCGCTATCAAATTATTACATTCTTAATTGCCGGACACGTAACAACAAGTGGTCTT
TTATCATTTGCGCTGTATTTCTTAGTGAAAAATCCACATGTATTACAAAAGCAGCAGAAGAA
GCAGCACGAGTTCTAGTAGATCCTGTTCCAAGCTACAAACAAGTCAAACAGCTTAAATATGTC
GGCATGGTCTTAAACGAAGCGCTGCGCTTATGGCCAACTGCTCCTGCGTTTTCCCTATATGCA
AAAGAAGATACGGTGCTTGGAGGAGAATATCCTTTAGAAAAAGGCGACGAACTAATGGTTCTG
ATTCCTCAGCTTCACCGTGATAAAACAATTTGGGGAGACGATGTGGAAGAGTTCCGTCCAGAG
CGTTTTGAAAATCCAAGTGCGATTCCGCAGCATGCGTTTAAACCGTTTGGAAACGGTCAGCGT
GCGTGTATCGGTCAGCAGTTCGCTCTTCATGAAGCAACGCTGGTACTTGGTATGATGCTAAAA
CACTTTGACTTTGAAGATCATACAAACTACGAGCTCGATATTAAAGAAACTTTAACGTTAAAA
CCTGAAGGCTTTGTGGTAAAAGCAAAATCGAAAAAAATTCCGCTTGGCGGTATTCCTTCACCT
AGCACTGAACAGTCTGCTAAAAAAGTACGCAAAAAGGCAGAAAACGCTCATAATACGCCGCTG
CTTGTGCTATACGGTTCAAATATGGGAACAGCTGAAGGAACGGCGCGTGATTTAGCAGATATT
GCAATGAGCAAAGGATTTGCACCGCAGGTCGCAACGCTTGATTCACACGCCGGAAATCTTCCG
CGCGAAGGAGCTGTATTAATTGTAACGGCGTCTTATAACGGTCATCCGCCTGATAACGCAAAG
CAATTTGTCGACTGGTTAGACCAAGCGTCTGCTGATGAAGTAAAAGGCGTTCGCTACTCCGTA
TTTGGATGCGGCGATAAAAACTGGGCTACTACGTATCAAAAAGTGCCTGCTTTTATCGATGAA
ACGCTTGCCGCTAAAGGGGCAGAAAACATCGCTGACCGCGGTGAAGCAGATGCAAGCGACGAC
TTTGAAGGCACATATGAAGAATGGCGTGAACATATGTGGAGTGACGTAGCAGCCTACTTTAAC
CTCGACATTGAAAACAGTGAAGATAATAAATCTACTCTTTCACTTCAATTTGTCGACAGCGCC
GCGGATATGCCGCTTGCGAAAATGCACGGTGCGTTTTCAACGAACGTCGTAGCAAGCAAAGAA
CTTCAACAGCCAGGCAGTGCACGAAGCACGCGACATCTTGAAATTGAACTTCCAAAAGAAGCT
TCTTATCAAGAAGGAGATCATTTAGGTGTTATTCCTCGCAACTATGAAGGAATAGTAAACCGT
GTAACAGCAAGGTTCGGCCTAGATGCATCACAGCAAATCCGTCTGGAAGCAGAAGAAGAAAAA
TTAGCTCATTTGCCACTCGCTAAAACAGTATCCGTAGAAGAGCTTCTGCAATACGTGGAGCTT
CAAGATCCTGTTACGCGCACGCAGCTTCGCGCAATGGCTGCTAAAACGGTCTGCCCGCCGCAT
AAAGTAGAGCTTGAAGCCTTGCTTGAAAAGCAAGCCTACAAAGAACAAGTGCTGGCAAAACGT
TTAACAATGCTTGAACTGCTTGAAAAATACCCGGCGTGTGAAATGAAATTCAGCGAATTTATC
GCCCTTCTGCCAAGCATACGCCCGCGCTATTACTCGATTTCTTCATCACCTCGTGTCGATGAA
AAACAAGCAAGCATCACGGTCAGCGTTGTCTCAGGAGAAGCGTGGAGCGGATATGGAGAATAT
AAAGGAATTGCGTCGAACTATCTTGCCGAGCTGCAAGAAGGAGATACGATTACGTGCTTTATT
TCCACACCGCAGTCAGAATTTACGCTGCCAAAAGACCCTGAAACGCCGCTTATCATGGTCGGA
CCGGGAACAGGCGTCGCGCCGTTTAGAGGCTTTGTGCAGGCGCGCAAACAGCTAAAAGAACAA
GGACAGTCACTTGGAGAAGCACATTTATACTTCGGCTGCCGTTCACCTCATGAAGACTATCTG
TATCAAGAAGAGCTTGAAAACGCCCAAAGCGAAGGCATCATTACGCTTCATACCGCTTTTTCT
CGCATGCCAAATCAGCCGAAAACATACGTTCAGCACGTAATGGAACAAGACGGCAAGAAATTG
ATTGAACTTCTTGATCAAGGAGCGCACTTCTATATTTGCGGAGACGGAAGCCAAATGGCACCT
GCCGTTGAAGCAACGCTTATGAAAAGCTATGCTGACGTTCACCAAGTGAGTGAAGCAGACGCT
CGCTTATGGCTGCAGCAGCTAGAAGAAAAAGGCCGATACGCAAAAGACGTGTGGGCTGGGTAA-3′

Fig. 5

Amino acid sequence of wild-type CYP102A1 mutant #17 (M17)

| | |
|---|---|
| 1 | MTIKEMPQPKTFGELKNLPLLNTDKPVQALMKIADELGEIFKFEAPGLVTRYLSSQRLIK |
| 61 | EACDGSRFDKNLSQALKFVRDIAGDGLVTSWTHEKNWKKAHNILLPSFSQQAMKGYHAMM |
| 121 | VDIAVQLVQKWERLNADEHIEVPGDMTRLTLDTIGLCGFNYRFNSFYRDQPHPFITSMVR |
| 181 | ALDEAMNKQQRANPDDPAYDENKRQFQEDIKVMNDLVDKIIADRKASGEQSDDLLTHMLN |
| 241 | GKDPETGEPLDDENIRYQIITFLIAGHVTTSGLLSFALYFLVKNPHVLQKAAEEAARVLV |
| 301 | DPVPSYKQVKQLKYVGMVLNEALRLWPTAPAFSLYAKEDTVLGGEYPLEKGDELMVLIPQ |
| 361 | LHRDKTIWGDDVEEFRPERFENPSAIPQHAFKPFGNGQRACIGQQFALHEATLVLGMMLK |
| 421 | HFDFEDHTNYELDIKETLTLKPEGFVVKAKSKKIPLGGIPSPSTEQSAKKVRKKVENAHN |
| 481 | TPLLVLYGSNMGTAEGTARDLADIAMSKGFAPQVATLDSHAGNLPREGAVLIVTASYNGH |
| 541 | PPDNAKQFVDWLDQASADDVKGVRYSVFGCGDKNWATTYQKVPAFIDETLAAKGAENIAD |
| 601 | RGEADASDDFEGTYEEWREHMWSDVAAYFNLDIENSEDNKSTLSLQFVDSAADMPLAKMH |
| 661 | GAFSANVVASKELQQLGSERSTRHLEIALPKEASYQEGDHLGVIPRNYEGIVNRVTARFG |
| 721 | LDASQQIRLEAEEEKLAHLPLGKTVSVEELLQYVELQDPVTRTQLRAMAAKTVCPPHKVE |
| 781 | LEALLEKQAYKEQVLAKRLTMLELLEKYPACEMEFSEFIALLPSISPRYYSISSSPHVDE |
| 841 | KQASITVSVVSGEAWSGYGEYKGIASNYLANLQEGDTITCFVSTPQSGFTLPKDSETPLI |
| 901 | MVGPGTGVAPFRGFVQARKQLKEQGQSLGEAHLYFGCRSPHEDYLYQEELENAQNEGIIT |
| 961 | LHTAFSRVPNQPKTYVQHVMERDGKKLIELLDQGAHFYICGDGSQMAPDVEATLMKSYAD |
| 1021 | VYEVSEADARLWLQQLEEKGRYAKDVWAG- |

Fig. 6

5' -ATGACAATTAAAGAAATGCCTCAGCCAAAAACGTTTGGAGAGCTTAAAAATTTACCGTTATTA
AACACAGATAAACCGGTTCAAGCTTTGATGAAAATTGCGGATGAATTAGGAGAAATCTTTAAA
TTCGAGGCGCCTGGTCTTGTAACGCGCTACTTATCAAGTCAGCGTCTAATTAAAGAAGCATGC
GATGGATCACGCTTTGATAAAAACTTAAGTCAAGCGCTTAAATTTGTACGTGATATTGCAGGA
GACGGGTTAGTTACAAGCTGGACGCATGAAAAAAATTGGAAAAAAGCGCATAATATCTTACTT
CCAAGCTTCAGTCAGCAGGCAATGAAAGGCTATCATGCGATGATGGTCGATATCGCCGTGCAG
CTTGTTCAAAAGTGGGAGCGTCTAAATGCAGATGAGCATATTGAAGTACCGGGAGACATGACA
CGTTTAACGCTTGATACAATTGGTCTTTGCGGCTTTAACTATCGCTTTAACAGCTTTTACCGA
GATCAGCCTCATCCATTTATTACAAGTATGGTCCGTGCACTGGATGAAGCAATGAACAAGCAG
CAGCGAGCAAATCCAGACGACCCAGCTTATGATGAAAACAAGCGCCAGTTTCAAGAAGATATC
AAGGTGATGAACGACCTAGTAGATAAAATTATTGCAGATCGCAAAGCAAGCGGTGAACAAAGC
GATGATTTATTAACGCATATGCTAAACGGAAAAGATCCAGAAACGGGTGAGCCGCTTGATGAC
GAGAACATTCGCTATCAAATTATTACATTCTTAATTGCGGGACACGTAACAACAAGTGGTCTT
TTATCATTTGCGCTGTATTTCTTAGTGAAAAATCCACATGTATTACAAAAAGCAGCAGAAGAA
GCAGCACGAGTTCTAGTAGATCCTGTTCCAAGCTACAAACAAGTCAAACAGCTTAAATATGTC
GGCATGGTCTTAAACGAAGCGCTGCGCTTATGGCCAACTGCTCCTGCGTTTTCCCTATATGCA
AAAGAAGATACGGTGCTTGGAGGAGAATATCCTTTAGAAAAAGGCGACGAACTAATGGTTCTG
ATTCCTCAGCTTCACCGTGATAAAACAATTTGGGGAGACGATGTGGAAGAGTTCCGTCCAGAG
CGTTTTGAAAATCCAAGTGCGATTCCGCAGCATGCGTTTAAACCGTTTGGAAACGGTCAGCGT
GCGTGTATCGGTCAGCAGTTCGCTCTTCATGAAGCAACGCTGGTACTTGGTATGATGCTAAAA
CACTTTGACTTTGAAGATCATACAAACTACGAGCTCGATATTAAAGAAACTTTAACGTTAAAA
CCTGAAGGCTTTGTGGTAAAAGCAAAATCGAAAAAAATTCCGCTTGGCGGTATTCCTTCACCT
AGCACTGAACAGTCTGCTAAAAAAGTACGCAAAAAGGCAGAAAACGCTCATAATACGCCGCTG
CTTGTGCTATACGGTTCAAATATGGGAACAGCTGAAGGAACGGCGCGTGATTTAGCAGATATT
GCAATGAGCAAAGGATTTGCACCGCAGGTCGCAACGCTTGATTCACACGCCGGAAATCTTCCG
CGCGAAGGAGCTGTATTAATTGTAACGGCGTCTTATAACGGTCATCCGCCTGATAACGCAAAG
CAATTTGTCGACTGGTTAGACCAAGCGTCTGCTGATGAAGTAAAGGCGTTCGCTACTCCGTA
TTTGGATGCGGCGATAAAAACTGGGCTACTACGTATCAAAAAGTGCCTGCTTTTATCGATGAA
ACGCTTGCCGCTAAAGGGGCAGAAAACATCGCTGACCGCGGTGAAGCAGATGCAAGCGACGAC
TTTGAAGGCACATATGAAGAATGGCGTGAACATATGTGGAGTGACGTAGCAGCCTACTTTAAC
CTCGACATTGAAAACAGTGAAGATAATAAATCTACTCTTTCACTTCAATTTGTCGACAGCGCC
GCGGATATGCCGCTTGCGAAAATGCACGGTGCGTTTTCAACGAACGTCGTAGCAAGCAAAGAA
CTTCAACAGCCAGGCAGTGCACGAAGCACGCGACATCTTGAAATTGAACTTCCAAAAGAAGCT
TCTTATCAAGAAGGAGATCATTTAGGTGTTATTCCTCGCAACTATGAAGGAATAGTAAACCGT
GTAACAGCAAGGTTCGGCCTAGATGCATCACAGCAAATCCGTCTGGAAGCAGAAGAAGAAAAA
TTAGCTCATTTGCCACTCGCTAAAACAGTATCCGTAGAAGAGCTTCTGCAATACGTGGAGCTT
CAAGATCCTGTTACGCGCACGCAGCTTCGCGCAATGGCTGCTAAAACGGTCTGCCCGCCGCAT
AAAGTAGAGCTTGAAGCCTTGCTTGAAAAGCAAGCCTACAAAGAACAAGTGCTGGCAAAACGT
TTAACAATGCTTGAACTGCTTGAAAAATACCCGGCGTGTGAAATGAAATTCAGCGAATTTATC
GCCCTTCTGCCAAGCATACGCCCGCGCTATTACTCGATTTCTTCATCACCTCGTGTCGATGAA
AAACAAGCAAGCATCACGGTCAGCGTTGTCTCAGGAGAAGCGTGGAGCGGATATGGAGAATAT
AAAGGAATTGCGTCGAACTATCTTGCCGAGCTGCAAGAAGGAGATACGATTACGTGCTTTATT
TCCACACCGCAGTCAGAATTTACGCTGCCAAAAGACCCTGAAACGCCGCTTATCATGGTCGGA
CCGGGAACAGGCGTCGCGCCGTTTAGAGGCTTTGTGCAGGCGCGCAAACAGCTAAAAGAACAA
GGACAGTCACTTGGAGAAGCACATTTATACTTCGGCTGCCGTTCACCTCATGAAGACTATCTG
TATCAAGAAGAGCTTGAAAACGCCCAAAGCGAAGGCATCATTACGCTTCATACCGCTTTTTCT
CGCATGCCAAATCAGCCGAAAACATACGTTCAGCACGTAATGGAACAAGACGGCAAGAAATTG
ATTGAACTTCTTGATCAAGGAGCGCACTTCTATATTTGCGGAGACGGAAGCCAAATGGCACCT
GCCGTTGAAGCAACGCTTATGAAAAGCTATGCTGACGTTCACCAAGTGAGTGAAGCAGACGCT
CGCTTATGGCTGCAGCAGCTAGAAGAAAAAGGCCGATACGCAAAAGACGTGTGGGCTGGGTAA-3'

Fig. 7

Amino acid sequence of chimera M16A1V2 derived from wild-type CYP102A1 mutant #16 (M16)

| Position | Sequence |
|---|---|
| 1 | MTIKEMPQPKTFGELKNLPLLNTDKPVQALMKIADELGEIFKFEAPGRVTRYLSSQRLIK |
| 61 | EACDESRFDKNLSQALKFVRDFAGDGLFTSWTHEKNWKKAHNILLPSFSQQAMKGYHAMM |
| 121 | VDIAVQLVQKWERLNADEHIEVPEDMTRLTLDTIGLCGFNYRFNSFYRDQPHPFITSMVR |
| 181 | ALDEAMNKLQRANPDDPAYDENKRQFQEDIKVMNDLVDKIIADRKASGEQSDDLLTHMLN |
| 241 | GKDPETGEPLDDENIRYQIITFLIAGHETTSGLLSFALYFLVKNPHVLQKAAEEAARVLV |
| 301 | DPVPSYKQVKQLKYVGMVLNEALRLWPTAPAFSLYAKEDTVLGGEYPLEKGDELMVLIPQ |
| 361 | LHRDKTIWGDDVEEFRPERFENPSAIPQHAFKPFGNGQRACIGQQFALHEATLVLGMMLK |
| 421 | HFDFEDHTNYELDIKETLTLKPEGFVVKAKSKKIPLGGIPSPSTEQSAKKVRKKVENAHN |
| 481 | TPLLVLYGSNMGTAEGTARDLADIAMSKGFAPQVATLDSHAGNLPREGAVLIVTASYNGH |
| 541 | PPDNAKQFVDWLDQASADDVKGVRYSVFGCGDKNWATTYQKVPAFIDETLAAKGAENIAD |
| 601 | RGEADASDDFEGTYEEWREHMWSDVAAYFNLDIENSEDNKSTLSLQFVDSAADMPLAKMH |
| 661 | GAFSANVVASKELQQLGSERSTRHLEIALPKEASYQEGDHLGVIPRNYEGIVNRVTARFG |
| 721 | LDASQQIRLEAEEEKLAHLPLGKTVSVEELLQYVELQDPVTRTQLRAMAAKTVCPPHKVE |
| 781 | LEALLEKQAYKEQVLAKRLTMLELLEKYPACEMEFSEFIALLPSISPRYYSISSSPHVDE |
| 841 | KQASITVSVVSGEAWSGYGEYKGIASNYLANLQEGDTITCFVSTPQSGFTLPKDSETPLI |
| 901 | MVGPGTGVAPFRGFVQARKQLKEQGQSLGEAHLYFGCRSPHEDYLYQEELENAQNEGIIT |
| 961 | LHTAFSRVPNQPKTYVQHVMERDGKKLIELLDQGAHFYICGDGSQMAPDVEATLMKSYAD |
| 1021 | VYEVSEADARLWLQQLEEKGRYAKDVWAG- |

Fig. 8

5' -ATGACAATTAAAGAAATGCCTCAGCCAAAAACGTTTGGAGAGCTTAAAAATTTACCGTTATTA
AACACAGATAAACCGGTTCAAGCTTTGATGAAAATTGCGGATGAATTAGGAGAAATCTTTAAA
TTCGAGGCGCCTGGTCTTGTAACGCGCTACTTATCAAGTCAGCGTCTAATTAAAGAAGCATGC
GATGAATCACGCTTTGATAAAAACTTAAGTCAAGCGCTTAAATTTGTACGTGATATTGCAGGA
GACGGGTTAGTTACAAGCTGGACGCATGAAAAAAATTGGAAAAAGCGCATAATATCTTACTT
CCAAGCTTCAGTCAGCAGGCAATGAAAGGCTATCATGCGATGATGGTCGATATCGCCGTGCAG
CTTGTTCAAAAGTGGGAGCGTCTAAATGCAGATGAGCATATTGAAGTACCGGGAGACATGACA
CGTTTAACGCTTGATACAATTGGTCTTTGCGGCTTTAACTATCGCTTTAACAGCTTTTACCGA
GATCAGCCTCATCCATTTATTACAAGTATGGTCCGTGCACTGGATGAAGCAATGAACAAGCAG
CAGCGAGCAAATCCAGACGACCCAGCTTATGATGAAAACAAGCGCCAGTTTCAAGAAGATATC
AAGGTGATGAACGACCTAGTAGATAAAATTATTGCAGATCGCAAAGCAAGCGGTGAACAAAGC
GATGATTTATTAACGCATATGCTAAACGGAAAAGATCCAGAAACGGGTGAGCCGCTTGATGAC
GAGAACATTCGCTATCAAATTATTACATTCTTAATTGCGGGACACGTAACAACAAGTGGTCTT
TTATCATTTGCGCTGTATTTCTTAGTGAAAAATCCACATGTATTACAAAAAGCAGCAGAAGAA
GCAGCACGAGTTCTAGTAGATCCTGTTCCAAGCTACAAACAAGTCAAACAGCTTAAATATGTC
GGCATGGTCTTAAACGAAGCGCTGCGCTTATGGCCAACTGCTCCTGCGTTTTCCCTATATGCA
AAAGAAGATACGGTGCTTGGAGGAGAATATCCTTTAGAAAAAGGCGACGAACTAATGGTTCTG
ATTCCTCAGCTTCACCGTGATAAAACAATTTGGGGAGACGATGTGGAAGAGTTCCGTCCAGAG
CGTTTTGAAAATCCAAGTGCGATTCCGCAGCATGCGTTTAAACCGTTTGGAAACGGTCAGCGT
GCGTGTATCGGTCAGCAGTTCGCTCTTCATGAAGCAACGCTGGTACTTGGTATGATGCTAAAA
CACTTTGACTTTGAAGATCATACAAACTACGAGCTCGATATTAAAGAAACTTTAACGTTAAAA
CCTGAAGGCTTTGTGGTAAAAGCAAAATCGAAAAAAATTCCGCTTGGCGGTATTCCTTCACCT
AGCACTGAACAGTCTGCTAAAAAAGTACGCAAAAAGGTAGAAAACGCTCATAATACGCCGCTG
CTTGTGCTATACGGTTCAAATATGGGAACAGCTGAAGGAACGGCGCGTGATTTAGCAGATATT
GCAATGAGCAAAGGATTTGCACCGCAGGTCGCAACGCTTGATTCACACGCCGGAAATCTTCCG
CGCGAAGGAGCTGTATTAATTGTAACGGCGTCTTATAACGGTCATCCGCCTGATAACGCAAAG
CAATTTGTCGACTGGTTAGACCAAGCGTCTGCTGATGATGTAAAAGGCGTTCGCTACTCCGTA
TTTGGATGCGGCGATAAAAACTGGGCTACTACGTATCAAAAAGTGCCTGCTTTTATCGATGAA
ACGCTTGCCGCTAAAGGGGCAGAAAACATCGCTGACCGCGGTGAAGCAGATGCAAGCGACGAC
TTTGAAGGCACATATGAAGAATGGCGTGAACATATGTGGAGTGACGTAGCAGCCTACTTTAAC
CTCGACATTGAAAACAGTGAAGATAATAAATCTACTCTTTCACTTCAATTTGTCGACAGCGCC
GCGGATATGCCGCTTGCGAAAATGCACGGTGCGTTTTCAGCGAACGTCGTAGCAAGCAAAGAA
CTTCAACAGCTAGGCAGTGAACGAAGCACGCGACATCTTGAAATTGCACTTCCAAAAGAAGCT
TCTTATCAAGAAGGAGATCATTTAGGTGTTATTCCTCGCAACTATGAAGGAATAGTAAACCGT
GTAACAGCAAGGTTCGGCCTAGATGCATCACAGCAAATCCGTCTGGAAGCAGAAGAAGAAAAA
TTAGCTCATTTGCCACTCGGTAAAACAGTATCCGTAGAAGAGCTTCTGCAATACGTGGAGCTT
CAAGATCCTGTTACGCGCACGCAGCTTCGCGCAATGGCTGCTAAAACGGTCTGCCCGCCGCAT
AAAGTAGAGCTTGAAGCCTTGCTTGAAAAGCAAGCCTACAAAGAACAAGTGCTGGCAAAACGT
TTAACAATGCTTGAACTGCTTGAAAAATACCCGGCGTGTGAAATGGAATTCAGCGAATTTATC
GCCCTTCTGCCAAGCATAAGCCCGCGCTATTACTCGATTTCTTCATCACCTCATGTCGATGAA
AAACAAGCAAGCATCACGGTCAGCGTTGTCTCAGGAGAAGCGTGGAGCGGATATGGAGAATAT
AAAGGAATTGCGTCGAACTATCTTGCCGATCTGCAAGAAGGAGATACGATTACGTGCTTTGTT
TCCACACCGCAGTCAGGATTTACGCTGCCAAAAGACTCTGAAACGCCGCTTATCATGGTCGGA
CCGGGAACAGGCGTCGCGCCGTTTAGAGGCTTTGTGCAGGCGCGCAAACAGCTAAAAGAACAA
GGACAGTCACTTGGAGAAGCACATTTATACTTCGGCTGCCGTTCACCTCATGAAGACTATCTG
TATCAAGAAGAGCTTGAAAACGCCCAAAACGAAGGCATCATTACGCTTCATACCGCTTTTTCT
CGCGTGCCAAATCAGCCGAAAACATACGTTCAGCACGTAATGGAACGAGACGGCAAGAAATTG
ATTGAACTTCTTGATCAAGGAGCGCACTTCTATATTTGCGGAGACGGAAGCCAAATGGCACCT
GACGTTGAAGCAACGCTTATGAAAAGCTATGCTGACGTTTACGAAGTGAGTGAAGCAGACGCT
CGCTTATGGCTGCAGCAGCTAGAAGAAAAAGGCCGATACGCAAAAGACGTGTGGGCTGGGTAA-3'

Fig. 10
A
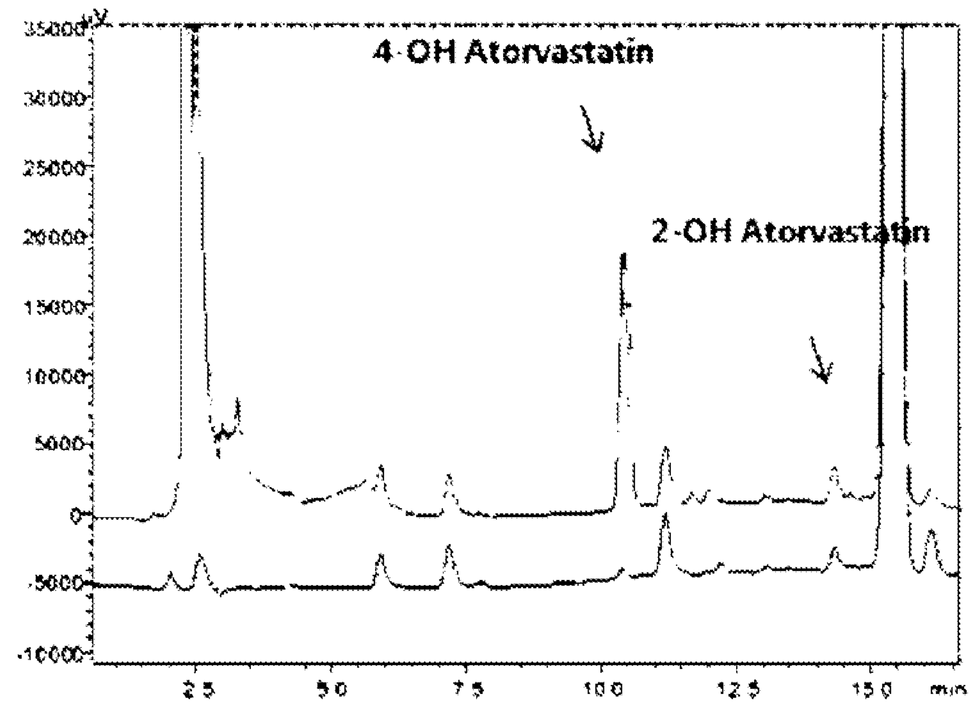
B
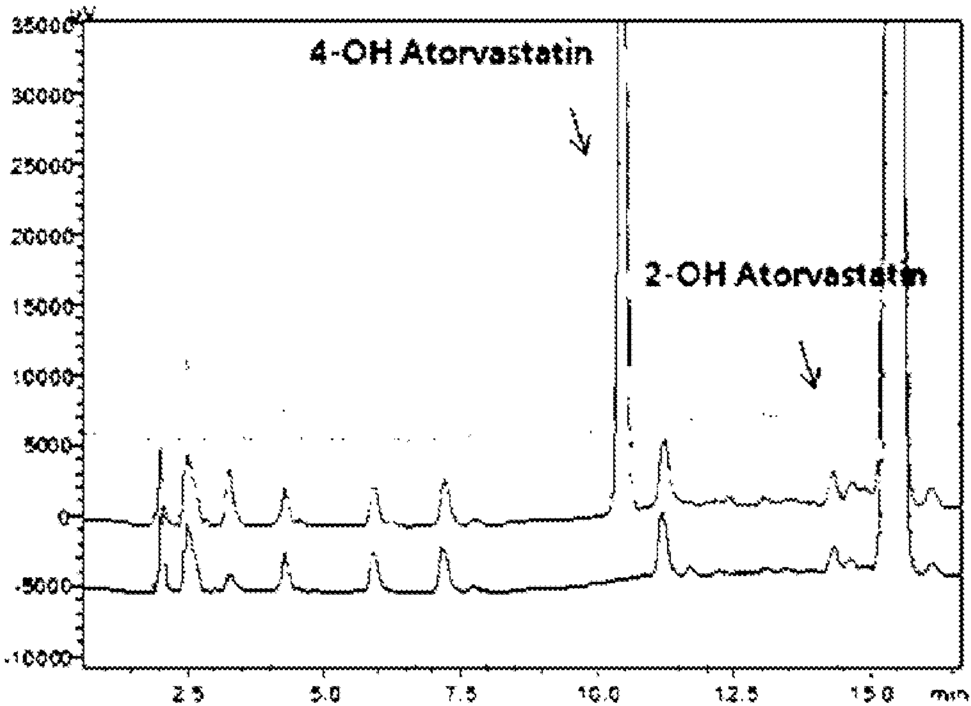

SEQUENCE LISTING

```
<160> NUMBER OF SEQ ID NOS: 23

<210> SEQ ID NO 1
<211> LENGTH: 31
<212> TYPE: DNA
<213> ORGANISM: Artificial Sequence
<220> FEATURE:
<223> OTHER INFORMATION: BamHI forward primer

<400> SEQUENCE: 1

agcggatcca tgacaattaa agaaatgcct c                                    31


<210> SEQ ID NO 2
<211> LENGTH: 20
<212> TYPE: DNA
<213> ORGANISM: Artificial Sequence
<220> FEATURE:
<223> OTHER INFORMATION: SacI reverse primer

<400> SEQUENCE: 2

atcgagctcg tagtttgtat                                                 20
```

<210> SEQ ID NO 3
<211> LENGTH: 20
<212> TYPE: DNA
<213> ORGANISM: Artificial Sequence
<220> FEATURE:
<223> OTHER INFORMATION: R47L primer

<400> SEQUENCE: 3
gcgcctggtc tggtaacgcg 20

<210> SEQ ID NO 4
<211> LENGTH: 21
<212> TYPE: DNA
<213> ORGANISM: Artificial Sequence
<220> FEATURE:
<223> OTHER INFORMATION: Y51F primer

<400> SEQUENCE: 4
gtaacgcgct tcttatcaag t 21

<210> SEQ ID NO 5
<211> LENGTH: 21
<212> TYPE: DNA
<213> ORGANISM: Artificial Sequence
<220> FEATURE:
<223> OTHER INFORMATION: E64G primer

<400> SEQUENCE: 5
gcatgcgatg gctcacgctt t 21

<210> SEQ ID NO 6
<211> LENGTH: 25
<212> TYPE: DNA
<213> ORGANISM: Artificial Sequence
<220> FEATURE:
<223> OTHER INFORMATION: A74G primer

<400> SEQUENCE: 6
taagtcaagg ccttaaattt gtacg 25

<210> SEQ ID NO 7
<211> LENGTH: 21
<212> TYPE: DNA
<213> ORGANISM: Artificial Sequence
<220> FEATURE:
<223> OTHER INFORMATION: F81I primer

<400> SEQUENCE: 7
gtacgtgata ttgcaggaga c 21

<210> SEQ ID NO 8
<211> LENGTH: 22
<212> TYPE: DNA
<213> ORGANISM: Artificial Sequence
<220> FEATURE:
<223> OTHER INFORMATION: L86I

<400> SEQUENCE: 8
ggagacggga tttttacaag ct 22

<210> SEQ ID NO 9
<211> LENGTH: 21
<212> TYPE: DNA
<213> ORGANISM: Artificial sequence
<220> FEATURE:
<223> OTHER INFORMATION: F87A primer

<400> SEQUENCE: 9
gacgggttag cgacaagctg g 21

<210> SEQ ID NO 10
<211> LENGTH: 21
<212> TYPE: DNA
<213> ORGANISM: Artificial sequence
<220> FEATURE:
<223> OTHER INFORMATION: F87V primer

<400> SEQUENCE: 10
gacgggttag tgacaagctg g 21

<210> SEQ ID NO 11
<211> LENGTH: 21
<212> TYPE: DNA
<213> ORGANISM: Artificial Sequence
<220> FEATURE:
<223> OTHER INFORMATION: E143G primer

<400> SEQUENCE: 11
gaagtaccgg gcgacatgac a 21

<210> SEQ ID NO 12
<211> LENGTH: 22
<212> TYPE: DNA
<213> ORGANISM: Artificial sequence
<220> FEATURE:
<223> OTHER INFORMATION: L188Q primer

<400> SEQUENCE: 12
atgaacaagc agcagcgagc aa 22

<210> SEQ ID NO 13
<211> LENGTH: 21
<212> TYPE: DNA
<213> ORGANISM: Artificial Sequence
<220> FEATURE:
<223> OTHER INFORMATION: A264G primer

<400> SEQUENCE: 13
ttcttaattg ggggacacgt g 21

<210> SEQ ID NO 14
<211> LENGTH: 22
<212> TYPE: DNA
<213> ORGANISM: Artificial sequence
<220> FEATURE:
<223> OTHER INFORMATION: E267V primer

<400> SEQUENCE: 14
tgcgggacac gtgacaacaa gt 22

<210> SEQ ID NO 15
<211> LENGTH: 23
<212> TYPE: DNA
<213> ORGANISM: Artificial sequence
<220> FEATURE:
<223> OTHER INFORMATION: L86I/F87V primer

<400> SEQUENCE: 15
ggagacggga ttgtgacaag ctg 23

<210> SEQ ID NO 16
<211> LENGTH: 1049

```
<212> TYPE: PRT
<213> ORGANISM: Artificial sequence
<220> FEATURE:
<223> OTHER INFORMATION: wild-type CYP102A1
<220> FEATURE:
<223> OTHER INFORMATION: CYP102A1 wild type

<400> SEQUENCE: 16

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
```

```
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800
```

```
Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 17
<211> LENGTH: 3150
<212> TYPE: DNA
<213> ORGANISM: Artificial sequence
<220> FEATURE:
<223> OTHER INFORMATION: wild type CYP102A1

<400> SEQUENCE: 17

```
atgacaatta aagaaatgcc tcagccaaaa acgtttggag agcttaaaaa tttaccgtta     60

ttaaacacag ataaaccggt tcaagctttg atgaaaattg cggatgaatt aggagaaatc    120

tttaaattcg aggcgcctgg tcgtgtaacg cgctacttat caagtcagcg tctaattaaa    180

gaagcatgcg atgaatcacg ctttgataaa aacttaagtc aagcgcttaa atttgtacgt    240

gattttgcag gagacgggtt atttacaagc tggacgcatg aaaaaaattg gaaaaaagcg    300

cataatatct tacttccaag cttcagtcag caggcaatga aaggctatca tgcgatgatg    360

gtcgatatcg ccgtgcagct tgttcaaaag tgggagcgtc taaatgcaga tgagcatatt    420

gaagtaccgg aagacatgac acgtttaacg cttgatacaa ttggtctttg cggctttaac    480

tatcgcttta acagctttta ccgagatcag cctcatccat ttattacaag tatggtccgt    540

gcactggatg aagcaatgaa caagctgcag cgagcaaatc cagacgaccc agcttatgat    600
```

```
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac    1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
```

```
ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150


<210> SEQ ID NO 18
<211> LENGTH: 1049
<212> TYPE: PRT
<213> ORGANISM: Artificial sequence
<220> FEATURE:
<223> OTHER INFORMATION: CYP102A1 mutant#16

<400> SEQUENCE: 18

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335
```

-continued

```
Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750
```

```
Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 19
<211> LENGTH: 3150
<212> TYPE: DNA
<213> ORGANISM: Artificial sequence
<220> FEATURE:
<223> OTHER INFORMATION: CYP102A1 mutant #16

<400> SEQUENCE: 19

```
atgacaatta aagaaatgcc tcagccaaaa acgtttggag agcttaaaaa tttaccgtta     60

ttaaacacag ataaaccggt tcaagctttg atgaaaattg cggatgaatt aggagaaatc    120

tttaaattcg aggcgcctgg tcttgtaacg cgctacttat caagtcagcg tctaattaaa    180

gaagcatgcg atgaatcacg ctttgataaa aacttaagtc aagcgcttaa atttgtacgt    240

gatattgcag gagacgggtt agttacaagc tggacgcatg aaaaaaattg gaaaaaagcg    300

cataatatct tacttccaag cttcagtcag caggcaatga aaggctatca tgcgatgatg    360
```

-continued

```
gtcgatatcg ccgtgcagct tgttcaaaag tgggagcgtc taaatgcaga tgagcatatt    420
gaagtaccgg gagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagcagcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgtaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac    1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
```

```
ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150
```

<210> SEQ ID NO 20
<211> LENGTH: 1049
<212> TYPE: PRT
<213> ORGANISM: Artificial sequence
<220> FEATURE:
<223> OTHER INFORMATION: CYP102A1 mutant #17

<400> SEQUENCE: 20

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Arg Tyr Leu Ser Ser Gln Arg Leu Ile Lys Glu Ala Cys Asp
    50                  55                  60

Gly Ser Arg Phe Asp Lys Asn Leu Ser Gln Ala Leu Lys Phe Val Arg
65                  70                  75                  80

Asp Ile Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Gly
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Gln Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Val Thr Thr Ser Gly
            260                 265                 270

Leu Leu Ser Phe Ala Leu Tyr Phe Leu Val Lys Asn Pro His Val Leu
        275                 280                 285
```

```
Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
            660                 665                 670

Leu Gln Gln Leu Gly Ser Glu Arg Ser Thr Arg His Leu Glu Ile Ala
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
```

```
705                 710                 715                 720

Leu Asp Ala Ser Gln Gln Ile Arg Leu Glu Ala Glu Glu Glu Lys Leu
                725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Ile Ser Pro Arg Tyr Tyr Ser Ile
            820                 825                 830

Ser Ser Ser Pro His Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Arg Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Asp Val  Glu Ala Thr Leu Met  Lys Ser Tyr Ala Asp  Val Tyr Glu
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045


<210> SEQ ID NO 21
<211> LENGTH: 3150
<212> TYPE: DNA
<213> ORGANISM: Artificial sequence
<220> FEATURE:
<223> OTHER INFORMATION: CYP102A1 mutant #17

<400> SEQUENCE: 21

atgacaatta aagaaatgcc tcagccaaaa acgtttggag agcttaaaaa tttaccgtta      60

ttaaacacag ataaaccggt tcaagctttg atgaaaattg cggatgaatt aggagaaatc     120
```

```
tttaaattcg aggcgcctgg tcttgtaacg cgctacttat caagtcagcg tctaattaaa    180
gaagcatgcg atggatcacg ctttgataaa aacttaagtc aagcgcttaa atttgtacgt    240
gatattgcag gagacgggtt agttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg gagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagcagcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgtaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
```

```
aaacaagcaa gcatcacggt cagcgttgtc tcaggagaag cgtggagcgg atatggagaa   2580

tataaaggaa ttgcgtcgaa ctatcttgcc gagctgcaag aaggagatac gattacgtgc   2640

tttatttcca caccgcagtc agaatttacg ctgccaaaag accctgaaac gccgcttatc   2700

atggtcggac cgggaacagg cgtcgcgccg tttagaggct ttgtgcaggc gcgcaaacag   2760

ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150
```

```
<210> SEQ ID NO 22
<211> LENGTH: 1049
<212> TYPE: PRT
<213> ORGANISM: Artificial sequence
<220> FEATURE:
<223> OTHER INFORMATION: chimera #16A1V2

<400> SEQUENCE: 22

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
```

```
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
            660                 665                 670
```

```
Leu Gln Gln Leu Gly Ser Glu Arg Ser Thr Arg His Leu Glu Ile Ala
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Ile Ser Pro Arg Tyr Tyr Ser Ile
            820                 825                 830

Ser Ser Ser Pro His Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Arg Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                 1005

Asp Val  Glu Ala Thr Leu Met  Lys Ser Tyr Ala Asp  Val Tyr Glu
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045
```

<210> SEQ ID NO 23
<211> LENGTH: 3150
<212> TYPE: DNA
<213> ORGANISM: Artificial sequence
<220> FEATURE:

<223> OTHER INFORMATION: chimera #16A1V2

<400> SEQUENCE: 23

```
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcttgtaacg cgctacttat caagtcagcg tctaattaaa    180
gaagcatgcg atgaatcacg ctttgataaa aacttaagtc aagcgcttaa atttgtacgt    240
gatattgcag gagacgggtt agttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg gagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagcagcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgtaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggtagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgatgta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac     1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt cagcgaacgt cgtagcaagc aaagaacttc aacagctagg cagtgaacga   2040
agcacgcgac atcttgaaat tgcacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcggtaaaa cagtatccgt agaagagctt ctgcaatacg tggagcttca agatcctgtt   2280
```

-continued

```
acgcgcacgc agcttcgcgc aatggctgct aaaacggtct gcccgccgca taaagtagag   2340

cttgaagcct tgcttgaaaa gcaagcctac aaagaacaag tgctggcaaa acgtttaaca   2400

atgcttgaac tgcttgaaaa atacccggcg tgtgaaatgg aattcagcga atttatcgcc   2460

cttctgccaa gcataagccc gcgctattac tcgatttctt catcacctca tgtcgatgaa   2520

aaacaagcaa gcatcacggt cagcgttgtc tcaggagaag cgtggagcgg atatggagaa   2580

tataaaggaa ttgcgtcgaa ctatcttgcc gatctgcaag aaggagatac gattacgtgc   2640

tttgtttcca caccgcagtc aggatttacg ctgccaaaag actctgaaac gccgcttatc   2700

atggtcggac cgggaacagg cgtcgcgccg tttagaggct ttgtgcaggc gcgcaaacag   2760

ctaaaagaac aaggacagtc acttggagaa gcacatttat acttcggctg ccgttcacct   2820

catgaagact atctgtatca agaagagctt gaaaacgccc aaaacgaagg catcattacg   2880

cttcataccg ctttttctcg cgtgccaaat cagccgaaaa catacgttca gcacgtaatg   2940

gaacgagacg gcaagaaatt gattgaactt cttgatcaag gagcgcactt ctatatttgc   3000

ggagacggaa gccaaatggc acctgacgtt gaagcaacgc ttatgaaaag ctatgctgac   3060

gtttacgaag tgagtgaagc agacgctcgc ttatggctgc agcagctaga agaaaaaggc   3120

cgatacgcaa aagacgtgtg ggctgggtaa                                     3150
```

METHOD FOR PREPARING METABOLITES OF ATORVASTATIN USING BACTERIAL CYTOCHROME P450 AND COMPOSITION THEREFOR

TECHNICAL FIELD

The present invention relates to a novel method for preparing metabolites of atorvastatin using bacterial cytochrome P450 and a composition therefor.

BACKGROUND ART

Atorvastatin is well known as an anti-hyperlipidemic agent, an antihypercholesterolemic agent, or a cholesterol-lowering agent. Oxidative metabolism of atorvastatin in human liver is mediated by mainly cytochrome P450 3A (CYP3A) enzymes, particularly, cytochrome P450 3A4 (CYP3A4), and the following two metabolites, that is, ortho-hydroxy atorvastatin (ortho-OH atorvastatin or 2-OH atorvastatin) and parahydroxy atorvastatin (para-OH atorvastatin or 4-OH atorvastatin) are generated.

HMG-CoA reductase catalyzes the conversion of HMG-CoA to mevalonate, which is an early and rate-limiting step in the biosynthesis of cholesterol.

In addition to the P450-mediated oxidation and β-oxidation processes, glucuronidation constitutes a common metabolic pathway for statins (Prueksaritanont et al., Drug Metab. Dispos. 30:505-512, 2002). The metabolites resulting from microsomal oxidation of atorvastatin by P450 enzymes are effective inhibitors of HMG-CoA reductase. In addition, it has been suggested that the metabolites may contribute to the cholesterol-lowering effect of atorvastatin.

Cytochrome P450 enzymes (P450s or CYPs) are large families consisting of enzymes serving as remarkably diverse oxygenation catalysts in throughout nature from archaea, bacteria, fungi, plants, and animals up to humans (http://drnelson.uthsc.edu/CytochromeP450.html). Due to the catalytic diversity and broad substrate range of P450s, they are attractive biocatalyst candidates for the production of fine chemicals, including pharmaceuticals.

However, in spite of the potential use of mammalian P450s in various biotechnology fields, they are not suitable as biocatalysts because of their low stability, low catalytic activity, and low affordability.

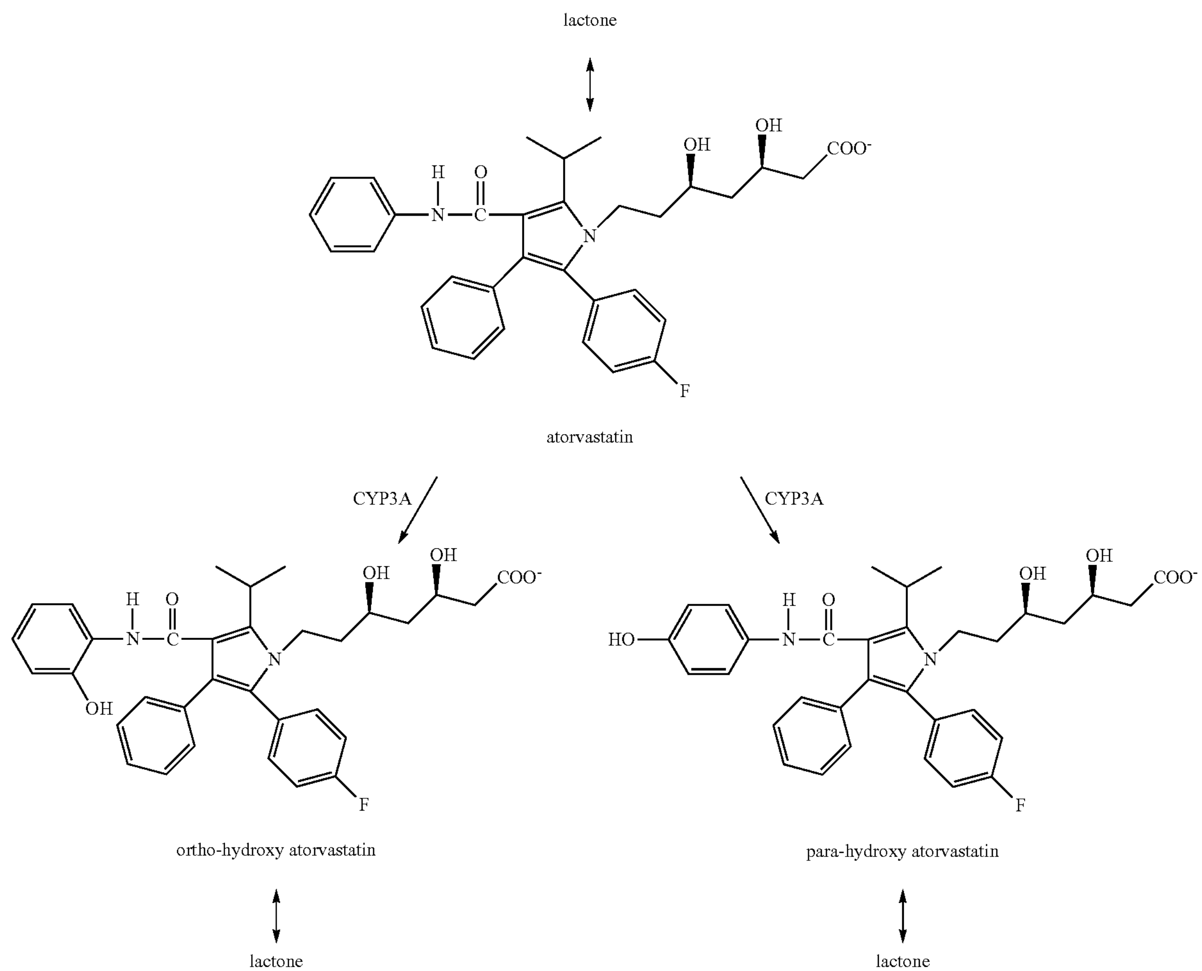

After oral ingestion, atorvastatin, which is an inactive lactone, is hydrolyzed to the corresponding β-hydroxy acid form. This is a main metabolite and an inhibitor of 3-hydroxy-3-methylglutaryl coenzyme A (HMG-CoA) reductase.

In the case in which a pro-drug is converted into a biologically "active metabolite" by human hepatic P450s during drug development, a large amount of pure metabolites are required in order to research into effect, toxicity, pharmacokinetics of the drug, or the like. Further, in the case in which the metabolite itself has biological activity, it may be advantageous to directly administer the metabolite to the body. Therefore, it is important to prepare the metabolite on a large scale.

However, since there are various problems in chemically synthesizing pure metabolites, P450 may be used in order to prepare the metabolites of a drug or drug candidates as an alternative for chemical synthesis of the metabolites. The metabolite preparation has been reported using human P450s expressed in *Escherichia coli* (Yun et al., Curr. Drug Metab. 7:411-429, 2006) and in insect cells (Rushmore et al., Metab. Eng. 2:115-125, 2000; Vail et al., J. Ind. Microbiol. Biotechnol. 32:67-74. 2005).

However, since these systems are still costly and have low productivities due to limited stabilities and slow reaction rates, a method of using engineered bacterial P450 enzymes having the desired catalyst activity has been suggested as an alternative for producing human metabolite.

Meanwhile, P450 BM3 (CYP102A1) from *Bacillus megaterium* has strong similarity to eukaryotic members of the CYP4A (fatty acid hydroxylase) family. It has been reported that CYP102A1 mutants oxidizes several human P450 substrates to produce the metabolite with higher activity (Kim et al., Protein Expr. Purif. 57:188-200, 2008a). Further, CYP102A1 is a versatile monooxygenase capable of working on various substrates (Di Nardo et al., J. Biol. Inorg. Chem. 12:313-323, 2007).

Recently, it has been reported that CYP102A1 mutants may produce larger quantities of the human metabolites of drugs, which may be difficult to be synthesized (Otey et al., Biotechnol. Bioeng. 93:494-499, 2005). Therefore, as an alternative method of preparing the metabolites, it may be considered to use CYP102A1 engineered so as to have the desired properties.

Several amino acid residues in CYP102A1 were mutated to generate mutant enzymes having increased activity toward human P450 substrates by the present inventors (Yun et al., Trends Biotechnol. 25:289-298, 2007 and other references cited in the article), and it was confirmed that specific mutants among these mutant enzymes may enable the CYP102A1 enzyme to catalyze O-deethylation and 3-hydroxylation of 7-ethoxycoumarin (Kim et al. Drug Metab. Dispos. 36:2166-2170, 2008a).

Therefore, while conducting research for directly using the atorvastatin metabolites as a drug, the present inventors discovered bacterial enzymes capable of oxidizing atorvastatin, which is known as a human P450 substrate, to produce 2-hydroxylated product and 4-hydroxylated product, which are human metabolites, and a biological preparation method using the same, thereby completing the present invention.

DISCLOSURE OF INVENTION

Technical Problem

An object of the present invention is to provide a bacterial enzyme capable of oxidizing atorvastatin to preparing 4-hydroxylated product or 2-hydroxylated product, which are human metabolites, on a large scale.

In addition, another object of the present invention is to provide a composition for preparing 2-hydroxylated product or 4-hydroxylated product from atorvastatin containing the enzyme.

Further, another object of the present invention is to provide a method for preparing 2-hydroxylated product or 4-hydroxylated product from atorvastatin including reacting the enzyme with atorvastatin.

Furthermore, another object of the present invention is to provide a kit for preparing 2-hydroxylated product or 4-hydroxylated product from atorvastatin containing the enzyme and a reduced nicotinamide adenine dinucleotide phosphate (NADPH)-generating system.

Solution to Problem

In one general aspect, there is provided a preparation method capable of selectively preparing human metabolites, particularly 2-hydroxylated product or 4-hydroxylated product from atorvastatin on a large scale using wild-type CYP102A1, CYP102A1 mutants, or chimeras derived from CYP102A1 mutants as a bacterial P450 enzyme, and a composition and a kit therefor.

In the present invention, "the CYP102A1 mutants" have an amino acid sequence of the wild-type CYP102A1 modified by natural or artificial substitution, deletion, addition, and/or insertion. Preferably, amino acid of the CYP102A1 mutant may be substituted with an amino acid that has similar properties as classified below. For example, alanine, valine, leucine, isoleucine, proline, methionine, phenylalanine, and tryptophan are classified as nonpolar amino acids and have similar properties to each other. Glycine, serine, threonine, cysteine, tyrosine, asparagine, and glutamine are neutral amino acids, aspartic acid and glutamic acid are acidic amino acids, and lysine, arginine, and histidine are basic amino acids.

The CYP102A1 mutants according to the present invention include polypeptide having an amino acid sequence similar to an amino acid sequence of CYP102A1 at an identity level of 50% or more, preferably, 75% or more, and more preferably, 90% or more.

In the present invention, the terms "chimeric" is used in the case in which at least two binding domains that are different from each other are contained therein. The two binding domains may be derived from different wild-type proteins. The two domains may be derived from the same wild-type protein, but in chimeric protein according to the present invention, the two domains may be positioned in a different arrangement from the corresponding the wild-type CYP102A1 mutant protein by fusing a heme domain of the wild-type CYP102A1 and a reductase domain of natural variants of the wild-type CYP102A1 to each other.

Hereinafter, the present invention will be described in detail.

The wild-type CYP102A1, the CYP102A1 mutant, or the chimera derived from the CYP102A1 mutant may be used as a catalyst in oxidation reaction using atorvastatin that is known as a human P450 substrate as the substrate.

More specifically, the present inventors clarified that the wild-type CYP102A1, the CYP102A1 mutant, or the chimera derived from the CYP102A1 mutant may be used as a catalyst in oxidation reaction using atorvastatin that is known as a human P450 substrate as the substrate. Particularly, in the case in which human CYP3A4 is used as the catalyst, as the produced atorvastatin metabolites, 2-hydroxylated product and 4-hydroxylated product may not be selectively produced. On the other hand, in the case in which the wild-type CYP102A1 mutant and the chimeras derived from the CYP102A1 according to the present invention are used as the catalyst, large amounts of 2-hydroxylated product and 4-hydroxylated product may be selectively and stably produced.

The present inventors prepared chimeras (#16A1V2, #17A1V2) derived from the CYP102A1 by selecting several mutants (wild-type CYP102A1 mutants #16 and #17 shown in Tables 2 and 3) with high catalytic activity for some substrates in a human among mutants prepared by over-expressing bacterial wild-type CYP102A1 and site-directed mutants thereof in *E. coli* (See Table 1) and fusing heme domains thereof and reductase domains of natural variants of the wild-type CYP102A1 to each other.

In the case in which the bacterial wild-type CYP102A1, the prepared mutants thereof (wild-type CYP102A1 mutants #16 and #17 shown in Tables 2 and 3), and chimeras (#16A1V2, #17A1V2) derived from the CYP102A1 was over-expressed in *E. coli* to be reacted with atorvastatin and a NADPH-generating system, it was confirmed that atorvastatin is converted into metabolites in humans through high-performance liquid chromatography (HPLC) (See FIG. 9) and a liquid chromatography-mass spectrometry (LC-MS) spectrum (See FIGS. 11 and 12).

In the case in which human CYP3A4 is used as the catalyst, as the produced atorvastatin metabolites, 2-hydroxylated product and 4-hydroxylated product may not be selectively produced. On the other hand, it might be appreciated that in the case in which the wild-type CYP102A1 mutant and the chimeras derived from the CYP102A1 according to the present invention are used as the catalyst, 2-hydroxylated product and 4-hydroxylated product may be selectively prepared on a large scale.

In addition, it might be appreciated that three kinds of mutants (#15, #16, and #17 in Table 2) and five kinds of chimeras (#16A1V2, #16A1V3, #17A1V2, #17A1V3, and #17A1V8) derived from the mutants have a large turnover number among the wild-type CYP102A1 mutants and the chimeras derived from the wild-type CYP102A1 mutants in producing the metabolites of atorvastatin. Particularly, it might be appreciated that the chimera #16A1V2 derived from the CYP102A1 mutant #16 and the chimera #17A1V2 derived from the CYP102A1 mutant #17 have the most excellent turnover number. See FIG. 14.

Based on the experiment results as described above, the present invention provides a composition for preparing 2-hydroxylated product or 4-hydroxylated product from atorvastatin including at least one enzyme selected from a group consisting of the wild-type CYP102A1, the CYP102A1 mutants, and chimeras derived from the CYP102A1 mutants, wherein the CYP102A1 mutant has an amino acid sequence changed from that of the wild-type CYP102A1 by at least one substitution selected from a group consisting of substituting arginine (R) at the amino acid position 47 with an amino acid selected from a group consisting of alanine, valine, leucine, isoleucine, proline, methionine, phenylalanine, and tryptophan, substituting tyrosine (Y) at the amino acid position 51 with an amino acid selected from a group consisting of alanine, valine, isoleucine, proline, methionine, phenylalanine, and tryptophan, substituting glutamic acid (E) at the amino acid position 64 with an amino acid selected from a group consisting of glycine, serine, threonine, cysteine, tyrosine, asparagine, and glutamine, substituting alanine (A) at the amino acid position 74 with an amino acid selected from a group consisting of glycine, serine, threonine, cysteine, tyrosine, asparagine, and glutamine, substituting phenylalanine (F) at the amino acid position 81 with an amino acid selected from a group consisting of alanine, valine, leucine, isoleucine, proline, methionine, and tryptophan, substituting leucine (L) at the amino acid position 86 with an amino acid selected from a group consisting of alanine, valine, isoleucine, proline, methionine, phenylalanine, and tryptophan, substituting phenylalanine (F) at amino acid position 87 with an amino acid selected from a group consisting of alanine, valine, leucine, isoleucine, proline, methionine, and tryptophan, substituting glutamic acid (E) at the amino acid position 143 with an amino acid selected from a group consisting of glycine, serine, threonine, cysteine, tyrosine, asparagine, and glutamine, substituting leucine (L) at the amino acid position 188 with an amino acid selected from a group consisting of glycine, serine, threonine, cysteine, tyrosine, asparagine, and glutamine, and substituting glutamic acid (E) at the amino acid position 267 with an amino acid selected from a group consisting of alanine, valine, leucine, isoleucine, proline, methionine, phenylalanine, and tryptophan, and the chimera derived from the CYP102A1 mutant has an amino acid sequence changed from that of the reductase domain of the CYP102A1 mutant by at least one substitution selected from a group of substituting lysine (K) at the amino acid position 474 with threonine (T), substituting alanine (A) at the amino acid position 475 with valine (V), substituting glutamine (Q) at the amino acid position 513 with arginine (R), substituting arginine (R) at the amino acid position 526 with proline (P), substituting glutamine (Q) at the amino acid position 547 with glutamic acid (E), substituting glutamic acid (E) at the amino acid position 559 with aspartic acid (D), substituting leucine (L) at the amino acid position 590 with phenylalanine (F), substituting alanine (A) at the amino acid position 591 with serine (S), substituting aspartic acid (D) at the amino acid position 600 with glutamic acid (E), substituting valine (V) at the amino acid position 625 with leucine (L), substituting aspartic acid (D) at the amino acid position 632 with asparagine (N), substituting aspartic acid (D) at the amino acid position 638 with glutamic acid (E), substituting lysine (K) at the amino acid position 640 with alanine (A), substituting alanine (A) at the amino acid position 652 with serine (S), substituting glycine (G) at the amino acid position 661 with arginine (R), substituting threonine (T) at the amino acid position 665 with alanine (A), substituting glutamine (Q) at the amino acid position 675 with lysine (K), substituting proline (P) at the amino acid position 676 with leucine (L), substituting alanine (A) at the amino acid position 679 with glutamic acid, substituting glutamic acid (E) at the amino acid position 688 with alanine (A), substituting threonine (T) at the amino acid position 716 with alanine (A), substituting alanine (A) at the amino acid position 717 with threonine (T), substituting alanine (A) at the amino acid position 742 with glycine (G), substituting alanine (A) at the amino acid position 783 with valine (V), substituting alanine (A) at the amino acid position 796 with threonine (T), substituting lysine (K) at the amino acid position 814 with glutamic acid (E), substituting isoleucine (I) at the amino acid position 825 with methionine (M), substituting arginine (R) at the amino acid position 826 with serine (S), substituting arginine (R) at the amino acid position 837 with histidine (H), substituting glutamic acid (E) at the amino acid position 871 with asparagine (N), substituting isoleucine (I) at the amino acid position 882 with valine (V), substituting glutamic acid (E) at the amino acid position 888 with glycine (G), substituting aspartic acid (D) at the amino acid position 894 with glycine (G), substituting proline (P) at the amino acid position 895 with serine (S), substituting glycine (G) at the amino acid position 913 with serine (S), substituting glutamic acid (E) at the amino acid position 948 with lysine (K), substituting serine (S) at the amino acid position 955 with asparagine (N), substituting methionine (M) at the amino acid position 968 with valine (V), substituting glutamine (Q) at the amino acid position 971 with glutamic acid (E), substituting methionine (M) at the amino acid position 980 with valine (V), substituting glutamine (Q) at the amino acid position 982 with arginine (R), substituting alanine (A) at the amino acid position 1009 with aspartic acid (D), substituting aspartic acid (D) at the amino acid position 1020 with glutamic acid (E), substituting histidine (H) at the amino acid position 1022 with tyrosine (Y), substituting glutamine (Q) at the amino acid position 1023 with lysine (K) and glutamic acid (E), and substituting glycine (G) at the amino acid position 1040 with serine (S).

Further, in another general aspect, the present invention provides a method for preparing 2-hydroxylated product or 4-hydroxylated product from atorvastatin including reacting at least one enzyme selected from a group consisting of wild-type CYP102A1, CYP102A1 mutants, and chimeras derived from the CYP102A1 mutants with atorvastatin, wherein the CYP102A1 mutant has an amino acid sequence changed from that of the wild-type CYP102A1 by at least one substitution selected from a group consisting of substituting arginine (R) at the amino acid position 47 with an amino acid selected from a group consisting of alanine, valine, leucine, isoleucine, proline, methionine, phenylalanine, and tryptophan, substituting tyrosine (Y) at the amino acid position 51 with an amino acid selected from a group consisting of alanine, valine, isoleucine, proline, methionine, phenylalanine, and tryptophan, substituting glutamic acid (E) at the amino acid position 64 with an amino acid selected from a group consisting of glycine, serine, threonine, cysteine, tyrosine, asparagine, and glutamine, substituting alanine (A) at the amino acid position 74 with an amino acid selected from a group consisting of glycine, serine, threonine, cysteine, tyrosine, asparagine, and glutamine, substituting phenylalanine (F) at the amino acid position 81 with an amino acid is selected from a group consisting of alanine, valine, leucine, isoleucine, proline, methionine, and tryptophan, substituting leucine (L) at the amino acid position 86 with an amino acid selected from the group consisting of alanine, valine, isoleucine, proline, methionine, phenylalanine, and tryptophan, substituting phenylalanine (F) at the amino acid position 87 with an amino acid selected from a group consisting of alanine, valine, leucine, isoleucine, proline, methionine, and tryptophan, substituting glutamic acid (E) at the amino acid position 143 with an amino acid selected from a group consisting of glycine, serine, threonine, cysteine, tyrosine, asparagine, and glutamine, substituting leucine (L) with the amino acid position 188 with an amino acid selected from a group consisting of glycine, serine, threonine, cysteine, tyrosine, asparagine, and glutamine, and substituting glutamic acid (E) at the amino acid position 267 with an amino acid selected from a group consisting of alanine, valine, an leucine, isoleucine, proline, methionine, phenylalanine, and tryptophan, and the chimera derived from the CYP102A1 mutant has an amino acid sequence changed from that of the reductase domain of the CYP102A1 mutant by at least one substitution selected from a group of substituting lysine (K) at the amino acid position 474 of the of CYP102A1 mutant with threonine (T), substituting alanine (A) at the amino acid position 475 with valine (V), substituting glutamine (Q) at the amino acid position 513 with arginine (R), substituting arginine (R) at the amino acid position 526 with proline (P), substituting glutamine (Q) at the amino acid position 547 with glutamic acid (E), substituting glutamic acid (E) at the amino acid position 559 with aspartic acid (D), substituting leucine (L) at the amino acid position 590 with phenylalanine (F), substituting alanine (A) at the amino acid position 591 with serine (S), substituting aspartic acid (D) at the amino acid position 600 with glutamic acid (E), substituting valine (V) at the amino acid position 625 with leucine (L), substituting aspartic acid (D) at the amino acid position 632 with asparagine (N), substituting aspartic acid (D) at the amino acid position 638 with glutamic acid (E), substituting lysine (K) at the amino acid position 640 with alanine (A), substituting alanine (A) at the amino acid position 652 with serine (S), substituting glycine (G) at the amino acid position 661 with arginine (R), substituting threonine (T) at the amino acid position 665 with alanine (A), substituting glutamine (Q) at the amino acid position 675 with lysine (K), substituting proline (P) at the amino acid position 676 with leucine (L), substituting alanine (A) at the amino acid position 679 with glutamic acid, substituting glutamic acid (E) at the amino acid position 688 with alanine (A), substituting threonine (T) at the amino acid position 716 with alanine (A), substituting alanine (A) at the amino acid position 717 with threonine (T), substituting alanine (A) at the amino acid position 742 with glycine (G), substituting alanine (A) at the amino acid position 783 with valine (V), substituting alanine (A) at the amino acid position 796 with threonine (T), substituting lysine (K) at the amino acid position 814 with glutamic acid (E), substituting isoleucine (I) at the amino acid position 825 with methionine (M), substituting arginine (R) at the amino acid position 826 with serine (S), substituting arginine (R) at the amino acid position 837 with histidine (H), substituting glutamic acid (E) at the amino acid position 871 with asparagine (N), substituting isoleucine (I) at the amino acid position 882 with valine (V), substituting glutamic acid (E) at the amino acid position 888 with glycine (G), substituting aspartic acid (D) at the amino acid position 894 with glycine (G), substituting proline (P) at the amino acid position 895 with serine (S), substituting glycine (G) at the amino acid position 913 with serine (S), substituting glutamic acid (E) at the amino acid position 948 with lysine (K), substituting serine (S) at the amino acid position 955 with asparagine (N), substituting methionine (M) at the amino acid position 968 with valine (V), substituting glutamine (Q) at the amino acid position 971 with glutamic acid (E),) substituting methionine (M) at the amino acid position 980 with valine (V), substituting glutamine (Q) at the amino acid position 982 with arginine (R), substituting alanine (A) at the amino acid position 1009 with aspartic acid (D), substituting aspartic acid (D) at the amino acid position 1020 with glutamic acid (E), substituting histidine (H) at the amino acid position 1022 with tyrosine (Y), substituting glutamine (Q) at the amino acid position 1023 with lysine (K) and glutamic acid (E), and substituting glycine (G) at the amino acid position 1040 with serine (S).

According to the present invention, preparation of the CYP102A1 mutants may be performed using various methods known in the art such as a deletion mutation method (Kowalski D. et al., J. Biochem., 15, 4457), a PCT method, a Kunkel method, a site-directed mutation method, a DNA shuffling, a staggered extension process (StEP), an error-prone polymerase chain reaction (PCR) method, or the like.

According to the present invention, the CYP012A1 mutant may have an amino acid sequence changed from that of the wild-type CYP102A1 by at least one substitution selected from a group consisting of substituting arginine (R) at the amino acid position 47 with leucine (L), substituting tyrosine (Y) at the amino acid position 51 with phenylalanine (F), substituting glutamic acid (E) at the amino acid position 64 with glycine (G), substituting alanine (A) at the amino acid position 74 with glycine (G), substituting phenylalanine (F) at the amino acid position 81 with isoleucine (I), substituting leucine (L) at the amino acid position 86 with isoleucine (I), substituting phenylalanine (F) at the amino acid position 87 with valine (V), substituting glutamic acid (E) at the amino acid position 143 with glycine (G), substituting leucine (L) at the amino acid position 188 with glutamine (Q), and substituting glutamic acid (E) at the amino acid position 267 with valine (V).

The most preferable CYP102A1 mutant according to the present invention may have an amino acid substitution position and substituted amino acid in the wild-type CYP102A1 selected from a group consisting of F87A, R47L/Y51F, A74G/F87V/188Q, R47L/L86I/L188Q, R47L/F87V/188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V.

For example, in the CYP102A1 mutant, the amino acid substitution position and substituted amino acid in the wild-type CYP102A1 is F87A, which means that phenylalanine (F) at the amino acid position 87 in the wild-type CYP102A1 is substituted with valine (V). Hereinafter, all of the CYP102A1 mutants and the chimeras derived from the CYP102 A1 mutants may also be interpreted to have the same meaning as described above.

The most preferable chimera derived from the CYP102A1 mutant according to the present invention may have an amino acid substitution position and substituted amino acid in the CYP102A1 mutant selected from a group consisting of A475V/E559D/T665A/P676L/A679E/E688A/A742G/K814E/R826S/R837H/E871N/I882V/E888G/P895S/S955N/M968V/Q982R/A1009D/H1022Y/Q1023E, A475V/E559D/T665A/A679E/E688A/A742G/K814E/E871N/I882V/E888G/P895S/G913G/S955N/M968V/A1009D/H1022Y/Q1023E, K474T/A475V/A591S/D600E/V625L/D632N/K640A/T665A/A717T/A742G/A796T/K814E/I825M/I882V/E888/S955N/M968V/M980V/A1009D/D1020E/Q1023K/G1040S, K474T/A475V/R526P/Q547E/D600E/V625 L/D638E/K640A/G661R/T665A/Q675K/T716A/A717T/A742G/A783V/K814E/I825M/E871N/I882V/E888G/D894G/E948K/S955N/M968V/Q971E/A1009D/D1020E, K474T/A475V/Q513R/Q547E/D600E/V625L/D638E/K640A/G661R/T665A/Q675K/T716A/A717T/A742G/A783V/K814E/I825M/E871N/I882V/E888G/D894G/E948K/S 955N/M968V/A1009D/D1020E, K474T/A475V/Q547E/D600E/V625L/D638E/K640A/G661R/T665A/Q675K/T716A/A717T/A742G/A783V/K814E/I825M/E871N/I882V/E888G/D894G/E948K/S955N/M968V/A1009D/D1020E, and K474T/A475V/Q547E/L590F/D600E/V625L/D638E/K640A/G661R/T665A/Q675K/T716A/A717T/A742G/A783V/K814E/I825M/E871N/I882V/E888G/D894G/E948K/S955N/M968V/A1009D/D1020E.

Protein according to the present invention may be prepared using the methods known in the art. For example, protein may be prepared by genetic engineering techniques, peptide synthesis using solid-phase techniques (Merrifield, J. Am. Chem. Soc., 85:2149-2154 (1963)), or method of cleaving protein using peptidase.

Protein according to the present invention may be natural protein or may be prepared by a recombination of culturing cells transformed with DNA encoding CYP102A1 or mutants thereof and collecting the protein. Protein may be prepared by inserting nucleic acid molecules encoding protein according to the present invention into an expression vector, transforming the vector into a host cell, culturing the transformed host cell, and purifying protein expressed by the transformed host cell.

The vector may be, for example, plasmid, cosmid, a virus, or phage. As the host cell into which DNA in the vector is cloned or expressed, there may be a prokaryotic cell, a yeast cell, and a higher eukaryotic cell. Culture conditions such as a culture medium, a temperature, pH, and the like, may be selected by those skilled in the art without undue experiment. In general, principles, protocols, and techniques for maximizing productivity of the culture of cells may refer to Mammalian Cell Biotechnology: A Practical Approach, M. Butler, ed. (IRL Press, 1991).

The expression and cloning vector may generally include a promoter that is operationally linked to a nucleic acid sequence that encodes CYP102A1 or mutants thereof inducing the synthesis of mRNA. Various promoters that are recognized by host cells are known. A promoter suitable for a prokaryotic host cell may be a β-lactamase and lactose promoter system, alkali phosphatase, a tryptophan (trp) promoter system, and a hybrid promoter, for example, a tac promoter. In addition, the promoter used in bacterial systems may include a Shine-Dalgarno (S.D.) sequence operationally linked to DNA that encodes CYP102A1 mutants. An example of the promoter suitable for a yeast host cell may include 3-phosphooglycerate kinase or other glycosidase.

The method for preparing 2-hydroxyatorvastin or 4-hydroxylated product from atorvastatin according to the present invention may further include adding a NADPH-generating system.

The NADPH-generating system may include glucose 6-phosphate, NADP+, and yeast glucose 6-phosphate dehydrogenase, but is not limited thereto.

In the NADPH-generating system, in the case in which the wild-type CYP102A1, the CYP012A1 mutants, and the chimeras derived from the CYP102A1 mutants are reacted with atorvastatin together with each other, atorvastatin may be effectively converted into 2-hydroxylated product and 4-hydroxylated product at the same time.

In addition, the method for preparing 2-hydroxylated product or 4-hydroxylated product from atorvastatin according to the present invention may be performed at 0 to 40° C., and preferably, 30 to 40° C. At the time of oxidation reaction using atorvastatin as the substrate in vitro system, the catalytic activity is increased at this temperature, thereby making it possible to efficiently and selectively produce atorvastatin.

In another general aspect, the present invention provides a kit for preparing 2-hydroxylated product or 4-hydroxylated product from atorvastatin including at least one enzyme selected from a group consisting of the wild-type CYP102A1, the CYP102A1 mutants, and the chimeras derived from the CYP102A1 mutants and the NADPH-generating system, wherein the CYP102A1 mutant includes an amino acid substitution position and substituted amino acid in the wild-type CYP102A1 selected from a group consisting of F87A, R47L/Y51F, A74G/F87V/L188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V, and the chimera derived from the CYP102A1 mutant includes an amino acid substitution position and substituted amino acid in the CYP102A1 mutant selected from a group consisting of A475V/E559D/T665A/P676L/A679E/E688A/A742G/K814E/R826S/R837H/E871N/I882V/E888G/P895S/S955N/M968V/Q982R/A1009D/H1022Y/Q1023E, A475V/E559D/T665A/A679E/E688A/A742G/K814E/E871N/I882V/E888G/P895S/G913G/S955N/M968V/A1009D/H1022Y/Q1023E, K474T/A475V/A591S/D600E/V625L/D632N/K640A/T665A/A717T/A742G/A796T/K814E/I825M/I882V/E888/S955N/M968V/M980V/A1009D/D1020E/Q1023K/G1040S, K474T/A475V/R526P/Q547E/D600E/V625L/D638E/K640A/G661R/T665A/Q675K/T716A/A717T/A742G/A783V/K814E/I825M/E871N/I882V/E888G/D894G/E948K/S955N/M968V/Q971E/A1009D/D1020E, K474T/A475V/Q513R/Q547E/D600E/V625L/D638E/K640A/G661R/T665A/Q675K/T716A/A717T/A742G/A783V/K814E/I825M/E871N/I882V/E888G/D894G/E948K/S955N/M968V/A1009D/D1020E, K474T/A475V/Q547E/D600V625L/D638E/K640A/G661R/T665A/Q675K/T716A/A717T/A742G/A783V/K814E/I825M/E871N/I882V/E888G/D894G/E948K/S955N/M968V/A1009D/D1020E, and K474T/A475V/Q547E/L590F/D600E/V625L/D638E/K640A/G661R/T665A/Q675K/T716A/A717T/A742G/A783V/K814E/I825M/E871N/I882V/E888G/D894G/E948K/S955N/M968V/A1009D/D1020E.

The kit according to the present invention may further include a reagent required to progress the reaction.

The NADPH-generating system may include glucose 6-phosphate, NADP+, and yeast glucose 6-phosphate dehydrogenase, but is not limited thereto.

Advantageous Effects of Invention

As set forth above, the wild-type CYP102A1, the CYP102A1 mutants, and the chimeras derived from the CYP102A1 mutants according to the present invention may stably and efficiently serve as the catalyst in the reaction of converting atorvastatin into 2-hydroxylated product and 4-hydroxylated product, such that 2-hydroxylated product and 4-hydroxylated product may be environmentally-friendly and selectively prepared on a large scale.

The composition, the kit, and the method for preparing 2-hydroxylated product or 4-hydroxylated product according to the present invention includes the wild-type CYP102A1, the CYP102A1 mutants, or the chimeras derived from the CYP102A1 mutants, such that 2-hydroxylated product or 4-hydroxylated product may be economically, efficiently, and selectively prepared from atorvastatin on a large scale. Therefore, the present invention may contribute to developing novel drugs using the metabolites of atorvastatin.

BRIEF DESCRIPTION OF DRAWINGS

The above and other objects, features and advantages of the present invention will become apparent from the following description of preferred embodiments given in conjunction with the accompanying drawings, in which:

FIG. 1 shows an amino acid sequence (sequence No. 16) of a wild-type CYP102A1 according to an exemplary embodiment of the present invention;

FIG. 2 shows a nucleotide sequence (sequence No. 17) of a wild-type CYP102A1 according to another exemplary embodiment of the present invention;

FIG. 3 shows an amino acid sequence (sequence No. 18) of a wild-type CYP102A1 mutant #16 according to another exemplary embodiment of the present invention;

FIG. 4 shows a nucleotide sequence (sequence No. 19) of a wild-type CYP102A1 mutant #16 according to another exemplary embodiment of the present invention;

FIG. 5 shows an amino acid sequence (sequence No. 20) of a wild-type CYP102A1 mutant #17 according to another exemplary embodiment of the present invention;

FIG. 6 shows a nucleotide sequence (sequence No. 21 of a wild-type CYP102A1 mutant #17 according to another exemplary embodiment of the present invention;

FIG. 7 shows an amino acid sequence (sequence No. 22) of a chimera #16A1V2 derived from the wild-type CYP102A1 mutant #16 according to another exemplary embodiment of the present invention;

FIG. 8 shows a nucleotide sequence (sequence No. 23) of a chimera #16A1V2 derived from the wild-type CYP102A1 mutant #16 according to another exemplary embodiment of the present invention;

FIGS. 10A and 10B show high-performance liquid chromatography (HPLC) chromatograms (measuring UV absorbance at 260 nm) of atorvastatin metabolites produced by a CYP102A1 mutant (FIG. 10A) and a chimera (FIG. 10B) derived from a CYP102A1 mutant according to the exemplary embodiment of the present invention;

(A: 4-hydroxylated product, B: 2-hydroxylated product, C: atorvastatin)

Figure 13:
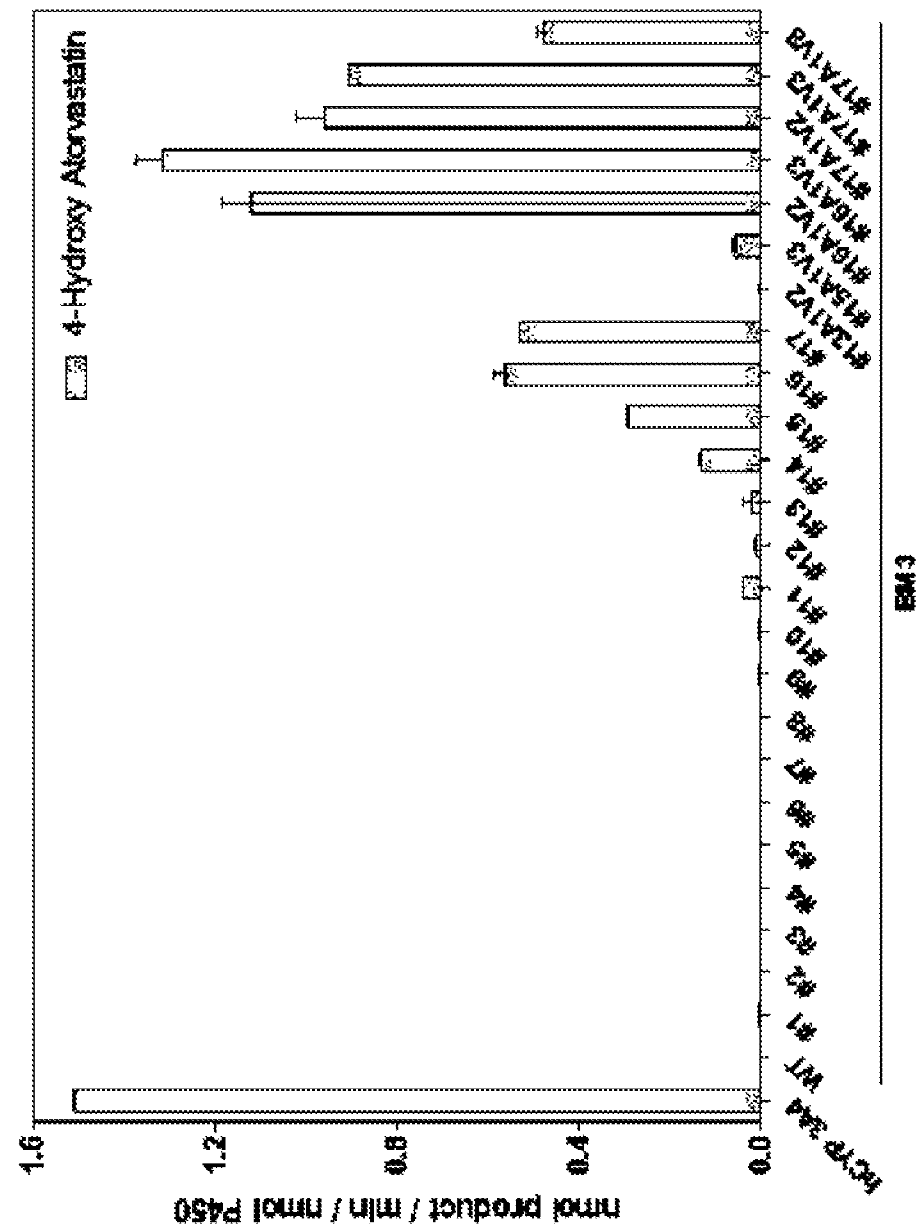
Figure 14:
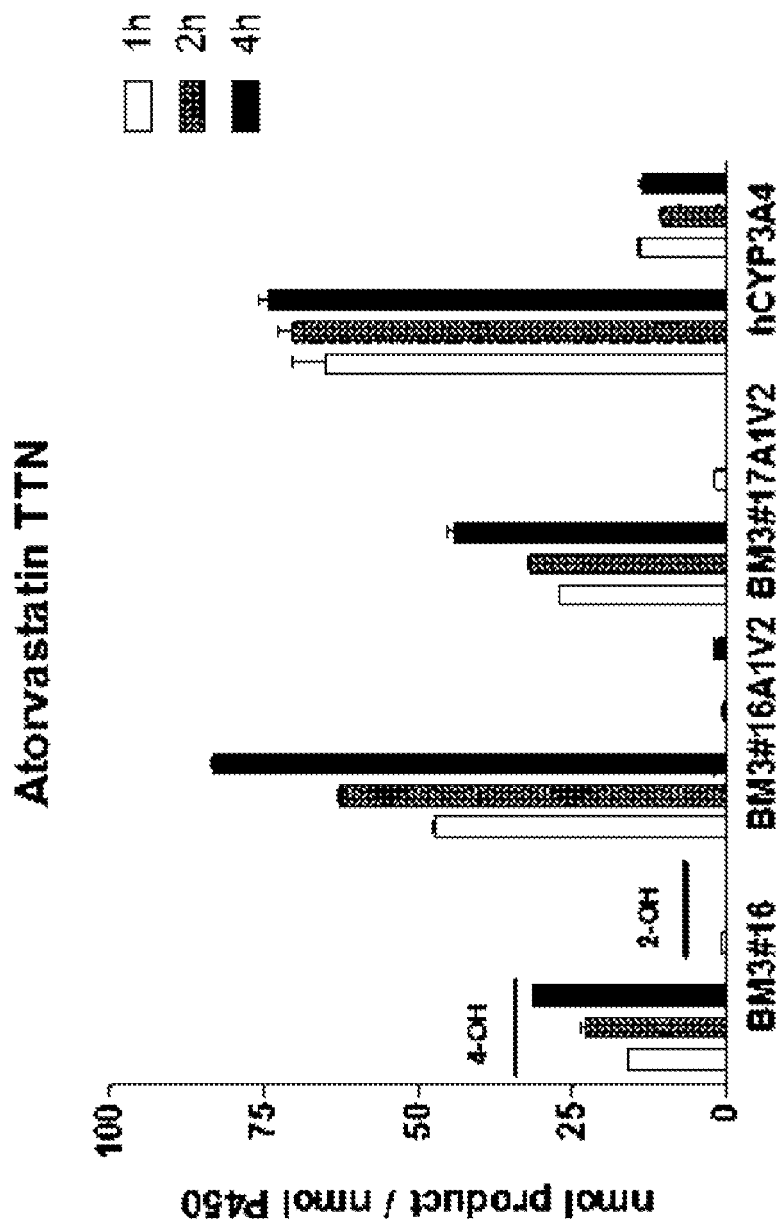

FIG. 13 shows turnover numbers of atorvastatin oxidation using the wild-type CYP102A1, mutants and the chimera derived from the CYP102A1 mutants according to the exemplary embodiment of the present invention; and FIG. 14 shows total turnover numbers (TTNs) of atorvastatin oxidation using chimeras derived from specific CYP102A1 mutants according to the exemplary embodiment of the present invention.

MODE FOR THE INVENTION

Hereinafter, exemplary embodiments of the present invention will be described in detail with reference to the accompanying drawings so that those skilled in the art may easily practice the present invention. However, the embodiment of the present invention has been disclosed for illustrative purposes, but the scopes of the present invention are not limited thereby.

EXAMPLE 1

Construction of P450 BM3 Mutants by Site-directed Mutagenesis 17 site-directed mutants of CYP102A1 were prepared by the same method as a method used by Kim et al., (Drug Metab. Dispos. 35: 2166-2170, 2008b). Primers used in order to introduce BanHI/SacI restriction sites and polymerase chain reaction (PCR) primers in order to introduce mutation were shown in the following Table 1. Codons for amino acid substitution were in italics and are underlined. The PCR primers were obtained from Genotech (Daejeon, Korea). Genes encoding the CYP102A1 mutants were amplified from pCWBM3 by PCR primers designed to facilitate cloning into an expression vector pCWori (Dr. F. W. Dahlquist, University of California, Santa Barbara, Calif.) or pSE420 (Invitrogen).

Oligonucleotide assembly was performed using the 14 sets of the designed primers shown in the following Table 1. The amplified genes were cloned into the BanHI/SacI restriction sites of the PCWBM3 BanHI/SacI vector. These plasmids were transformed into *Escherichia coli* DH5αF-IQ (Invitrogen), and this strain was also used to express the mutant CYP102A1 proteins. After mutagenesis, whether or not the desired mutations were generated was confirmed by DNA sequencing (Genotech, Daejeon, Korea).

TABLE 1

| Primers used to prepare mutants | |
|---|---|
| Name | Sequence |
| BamHI forward (sequence list 1) | 5' -AGC GGA TCC ATG ACA ATT AAA GAA ATG CCT C-3' |
| SacI reverse (sequence list 2) | 5' -ATC GAG CTC GTA GTT TGT AT-3' |
| R47L (sequence list 3) | 5' -GCG CCT GGT <u>CTG</u> GTA ACG CG-3' |
| Y51F (sequence list 4) | 5' -GTA ACG CGC <u>TTC</u> TTA TCA AGT-3' |
| E64G (sequence list 5) | 5' -GCA TGC GAT <u>GGC</u> TCA CGC TTT-3' |
| A74G (sequence list 6) | 5' -TA AGT CAA <u>GGC</u> CTT AAA TTT GTA CG-3' |
| F81I (sequence list 7) | 5' -GTA CGT GAT <u>ATT</u> GCA GGA GAC-3' |
| L861 (sequence list 8) | 5' -GGA GAC GGG <u>ATT</u> TTT ACA AGC T-3' |
| F87A (sequence list 9) | 5' -GAC GGG TTA <u>GCG</u> ACA AGC TGG-3' |
| F87V (sequence list 10) | 5' -GAC GGG TTA <u>GTG</u> ACA AGC TGG-3' |
| E143G (sequence list 11) | 5' -GAA GTA CCG <u>GGC</u> GAC ATG ACA-3' |
| L188Q (sequence list 12) | 5'-ATG AAC AAG <u>CAG</u> CAG CGA GCA A-3' |
| A264G (sequence list 13) | 5' -TTC TTA ATT <u>GGG</u> GGA CAC GTG-3' |
| E267V (sequence list 14) | 5' -T GCG GGA CAC <u>GTG</u> ACA ACA AGT-3' |

TABLE 1-continued

| Primers used to prepare mutants | |
|---|---|
| Name | Sequence |
| L861/F87V (sequence list 15) | 5' -GGA GAC GGG <u>ATT</u> <u>GTG</u> ACA AGC TG-3' |

EXAMPLE 2

Expression and Purification of Wild-type CYP102A1, Wild-type CYP102A1 Mutants, and Chimeras Derived from CYP012A1 Mutant Plasmids including genes of the Wild-type CYP102A1 (pCWBM3) and CYP102A1 mutant were transformed into *Escherichia coli* DH5αF-IQ (Kim et al., Drug Metab. Dispos. 35:2166-2170, 2008b). A culture was inoculated from a single colony into 5 ml of a Luria-Bertani medium supplemented with ampicillin (100 μg/ml) and grown at 37° C. This culture was inoculated into 250 ml of a Terrific Broth medium supplemented with ampicillin (100 μg/ml) and grown at 37° C. with shaking at 250 rpm so as to reach OD600 of about 0.8, and then gene expression was induced by the addition of isopropyl-β-D-thiogalactopyranoside to a final concentration of 0.5 mM. δ-Aminolevulinic acid (0.1 mM) was also added thereto. After inducing the expression, the culture was allowed to grow another 36 hours at 30° C., and then cells were harvested by centrifugation (15 min, 5000 g, 4° C.). The cell pellet was resuspended in a TES buffer solution (100 mM Tris-HCL, pH 7.6, 500 mM sucrose, 0.5 mM EDTA) and lysed by sonication (Sonicator; Misonix, Inc., Farmingdale. N.Y.). After the lysates was centrifuged at 100,000 g (90 min. 4° C.), a soluble cytosolic fraction was collected and used for the activity assay. The soluble cytosolic fraction was dialyzed from a 50 mM potassium phosphate buffer (pH 7.4) and stored at −80° C. The cytosolic fraction was used within 1 month of manufacture.

The CYP102A1 concentrations were determined from CO-difference spectra using $\epsilon$=91 mM/cm (Omura and Sato. J. Biol. Chem. 239:2370-2378, 1964). For all of the wild-types and mutants, a typical culture yielded 300 to 700 nM P450. The expression level of wild-type CYP102A1 and the mutants thereof were in the range of 1.0 to 2.0 nmol P450/mg cytosolic protein.

Several mutants with high catalytic activity for some substrates in human were selected among the prepared mutants, and the amino acid substitution sites in the mutants were shown in Tables 2 and 3.

[References]

Carmichael and Wong. Eur. J. Biochem. 268:3117-3125, 2001; Li et al., Appl. Environ. Microbiol. 67:5735-5739, 2001; van Vugt-Lussenburg et al., J. Med. Chem. 50:455-461, 2007

TABLE 2

| CYP102A1 mutants used in the present invention | | |
|---|---|---|
| Abbreviations | BM3 wild type and mutants | Ref |
| WT | BM3 wild type | Carmichael and Wong, 2001 |
| Mutant #1 | F87A | Carmichael and Wong, 2001 |
| Mutant #2 | A264G | Carmichael and Wong, 2001 |
| Mutant #3 | F87A/A264G | Carmichael and Wong, 2001 |
| Mutant #4 | R47L/Y51F | Carmichael and Wong, 2001 |
| Mutant #5 | R47L/Y51F/A264G | Carmichael and Wong, 2001 |
| Mutant #6 | R47L/Y51F/F87A | Carmichael and Wong, 2001 |
| Mutant #7 | R47L/Y51F/F87A/A264G | Carmichael and Wong, 2001 |
| Mutant #8 | A74G/F87V/L188Q | Li et al., 2001 |

TABLE 2-continued

| CYP102A1 mutants used in the present invention | | |
|---|---|---|
| Abbreviations | BM3 wild type and mutants | Ref |
| Mutant #9 | R47L/L86I/L188Q | Kim et al., 2008b |
| Mutant #10 | R47L/F87V/L188Q | van Vugt-Lussenburg et al., 2007 |
| Mutant #11 | R47L/F87V/L188Q/E267V | van Vugt-Lussenburg et al., 2007 |
| Mutant #12 | R47L/L86I/L188Q/E267V | Kim et al., 2008b |
| Mutant #13 | R47L/L86I/F87V/L188Q | van Vugt-Lussenburg et al., 2007 |
| Mutant #14 | R47L/F87V/E143G/L188Q/E267V | Kim et al., 2008b |
| Mutant #15 | R47L/E64G/F87V/E143G/L188Q/E267V | Kim et al., 2008b |
| Mutant #16 | R47L/F81I/F87V/E143G/L188Q/E267V | Kim et al., 2008b |
| Mutant #17 | R47L/E64G/F81I/F87V/E143G/L188Q/E267V | van Vugt-Lussenburg et al., 2007 |

TABLE 3

| CYP102A1 natural variants used in the present invention CYP102A1 Variants | | | | | | | | | | | |
|---|---|---|---|---|---|---|---|---|---|---|---|
| | Mutated Amino acid | Change of Nucleotide | *2 | *3 | *4 | *5 | *6 | *7 | *8 | *9 | QMB1551 |
| | T2P | 4A > C | | | | | | | | | + |
| Heme | V27I | 79G > A | + | | + | | + | + | + | + | + |
| domain | A29T | 85G > A | + | | + | | + | + | + | + | + |
| | V128I | 382G > A | + | | + | + | + | + | + | + | + |
| | A136T | 406G > A | + | | + | | + | + | + | + | + |
| | E208D | 624A > C | | | | + | | | | | |
| | A222T | 664G > A | | | | | | | | | + |
| | A296T | 886G > A | + | | + | | | | | | |
| | D370E | 1110C > A | + | | + | | | | | | |
| | K453Q | 1357A > C | | | | + | + | + | + | + | + |
| | T464R | 1392T > A | | | | + | + | + | + | + | + |
| | V471E | 1413A > G | | | | + | + | + | + | + | + |
| Reductase | K474T | 1422G > C | | | | + | + | + | + | + | + |
| domain | A475V | 1424C > T | + | + | + | + | + | + | + | + | + |
| | Q513R | 1539G > A | | | | | | + | | | |
| | R526P | 1578C > T | | | | | + | | | | |
| | Q547E | 1639C > G | | | | | + | + | + | + | + |
| | E559D | 1677A > C | + | + | + | | | | | | |
| | L590F | 1794C > A | | | | | | | | + | |
| | A591S | 1771G > T | | | | + | | | | | |
| | D600E | 1800C > A | | | | + | + | + | + | + | + |
| | V625L | 1873G > T | | | | + | + | + | + | + | + |
| | D632N | 1894G > A | | | | + | | | | | |
| | D638E | 1914T > A | | | | | + | + | + | + | + |
| | K640A | 1920A > T | | | | + | + | + | + | + | + |
| | A652S | 1954G > T | | | | | | | | | + |
| | G661R | 1981G > C | | | | | + | + | + | + | + |
| | T665A | 1993A > G | + | + | + | + | + | + | + | + | + |
| | Q675K | 2023C > A | | | | | + | + | + | + | + |
| | P676L | 2027C > T | + | + | | | | | | | |
| | A679E | 2036C > A | + | + | + | | | | | | |
| | E688A | 2063A > C | + | + | + | | | | | | |
| | T716A | 2146A > G | | | | | + | + | + | + | + |
| | A717T | 2149G > A | | | | + | + | + | + | + | + |
| | A742G | 2225C > G | + | + | + | + | + | + | + | + | + |
| | A783V | 2348C > T | | | | | + | + | + | + | + |
| | A796T | 2386G > A | | | | + | | | | | |
| | K814E | 2440A > G | + | + | + | + | + | + | + | + | + |
| | I825M | 2474A > G | | | | + | + | + | + | + | + |
| | R826S | 2476C > A | + | + | | | | | | | |
| | R837H | 2510G > A | + | + | | | | | | | |
| | E871N | 2613G > T | + | + | + | | + | + | + | + | + |
| | I882V | 2644A > G | + | + | + | + | + | + | + | + | + |
| | E888G | 2663A > G | + | + | + | + | + | + | + | + | + |
| | D894G | 2681A > G | | | | | + | + | + | + | + |
| | P895S | 2683C > T | + | + | + | | | | | | |
| | G913S | 2739C > T | | | + | | | | | | |
| | E948K | 2842G > A | | | | | + | + | + | + | + |
| | S955N | 2864G > A | + | + | + | + | + | + | + | + | + |
| | M968V | 2904G > A | + | + | + | + | + | + | + | + | + |
| | Q971E | 2911C > G | | | | | + | | | | |
| | M980V | 2938A > G | | | | + | | | | | |
| | Q982R | 2945A > G | + | + | | | | | | | |
| | A1009D | 3026C > A | + | + | + | + | + | + | + | + | + |
| | D1020E | 3060C > A | | | | + | + | + | + | + | + |

TABLE 3-continued

| CYP102A1 natural variants used in the present invention<br>CYP102A1 Variants | | | | | | | | | | |
|---|---|---|---|---|---|---|---|---|---|---|
| Mutated Amino acid | Change of Nucleotide | *2 | *3 | *4 | *5 | *6 | *7 | *8 | *9 | QMB1551 |
| H1022Y | 3066C > T | + | + | + | | | | | | |
| Q1023K | 3067C > G | | | | + | | | | | |
| Q1023E | 3067C > A | + | + | + | | | | | | |
| G1040S | 3118G > A | | | | + | | | | | |

In addition, a chimeric protein of selective CYP102A1 mutants was constructed by fusing heme domains of the prepared CYP102A1 mutants of Tables 2 and 3 to reductase domains of the natural variants of the wild-type CYP102A1.

In order to clone the chimeric protein of the selective CYP102A1 mutant prepared by fusing the heme domain and the reductase domain to each other, the chimeric protein was cloned into the expression vector pCW vector prepared using BanHI/SacI and SacI/XhoI.

Plasmids including genes of the chimeric protein of the CYP102A1 mutant were transformed into *Escherichia coli* DH5αF-IQ (Kim et al. Protein Expr. Purif. 57:188-200, 2008). A culture was inoculated from a single colony into 5 ml of a Luria-Bertani medium supplemented with ampicillin (100 μg/ml) and grown at 37° C. This culture was inoculated into 250 ml of a Terrific Broth medium supplemented with ampicillin (100 μg/ml) and grown at 37° C. with shaking at 250 rpm so as to reach OD600 of about 0.8, and then gene expression was induced by the addition of isopropyl-β-D-thiogalactopyranoside to a final concentration of 0.5 mM. δ-Aminolevulinic acid (0.1 mM) was also added thereto. After inducing of the expression, the culture was allowed to grow another 36 hours at 30° C., and then cells were harvested by centrifugation (15 min, 5000 g, 4° C.). The cell pellet was resuspended in a TES buffer solution (100 mM Tris-HCL, pH 7.6, 500 mM sucrose, 0.5 mM EDTA) and lysed by sonication (Sonicator. Misonix. Inc., Farmingdale. N.Y.). After the lysates was centrifuged at 100,000 g (90 min, 4° C.), a soluble cytosolic fraction was collected and used for the activity assay. The soluble cytosolic fraction was dialyzed from a 50 mM potassium phosphate buffer (pH 7.4) and stored at −80° C. The cytosolic fraction was used within 1 month of manufacture.

The CYP102A1 concentrations were determined from CO-difference spectra using $\epsilon$=91 mM/cm (Omura and Sato, J. Biol. Chem. 239:2379-2385 1964). For the chimeras derived from CYP102A1, a typical culture yielded 300 to 700 nM P450. The expression levels of the chimeras derived from the CYP102A1 mutant were in the range of 1.0 to 2.0 nmol P450/mg cytosolic protein.

Several chimeras with high catalytic activity for some substrates in a human were selected among the chimeras prepared from the CYP102A1 mutants, and the amino acid substitution sites in each chimera were shown in Table 4 (Kang et al., AMB Express, 1:1, 2011).

Hereinafter, the chimeras derived from the CYP102A1 mutants used in this experiment were called as follows.

In the present invention, the terms chimera #16A1V2 of the mutants means a chimera derived from a CYP102A1 mutant #16 prepared by fusing the heme domains of the mutant #16 in Table 2 to V2 reductase domain of the following Table 4.

TABLE 4

| CYP102A1 natural variants used in the present invention | | |
|---|---|---|
| Abbreviations | Natural variants | Ref |
| variant2(V2) | A475V/E559D/T665A/P676L/A679E/E688A/A742G/K814E/R826S/R837H/E871N/I882V/E888G/P895S/S955N/M968V/Q982R/A1009D/H1022Y/Q1023E | Kang et al. 2011 |
| variant3(V3) | A475V/E559D/T665A/P676L/A679E/E688A/A742G/K814E/R826S/R837H/E871N/I882V/E888G/P895S/S955N/M968V/Q982R/A1009D/H1022Y/Q1023E | Kang et al. 2011 |
| variant4(V4) | A475V/E559D/T665A/A679E/E688A/A742G/K814E/E871N/I882V/E888G/P895S/G913G/S955N/M968V/A1009D/H1022Y/Q1023E | Kang et al. 2011 |
| variant5(V5) | K474T/A475V/A591S/D600E/V625L/D632N/K640A/T665A/A717T/A742G/A796T/K814E/I825M/I882V/E888/S955N/M968V/M980V/A1009D/D1020E/Q1023E/G1040S | Kang et al. 2011 |
| variant6(V6) | K474T/A475V/R526P/Q547E/D600E/V625L/D638E/K640A/G661R/T665A/Q675K/T71GA/A717T/A742G/A783V/K814E/I825M/E871N/I882V/E888G/D894G/E948K/S955N/M968V/Q971E/A1009D/D1020E | Kang et al. 2011 |
| variant7(V7) | K474T/A475V/Q513R/Q547E/D600E/V625L/D638E/K640A/G661R/T665A/Q675K/T716A/A717T/A742G/A783V/K814E/I825M/E871N/I882V/E888G/D894G/E948K/S955N/M968V/A1009D/D1020E | Kang et al. 2011 |
| variant8(V8) | K474T/A475V/Q547E/D600E/V625L/D638E/K640A/G661R/T665A/Q675K/T716A/A717T/A742G/A783V/K814E/I825M/E87IN/I882V/E888G/D894G/E948K/S955N/M968V/A1009D/D1020E | Kang et al. 2011 |
| variant9(V9) | K474T/A475V/Q547E/L590F/D600E/V625L/D638E/K640A/G661R/T665A/Q675K/T716A/A717T/A742G/A783V/K814E/I825M/E871N/I882V/R888G/D894G/E948K/S955N/M968V/A1009D/D1U20E | Kang et al. 2011 |

EXAMPLE 3

Oxidation of Atorvastatin by Wild-type CYP102A1, Wild-type CYP102A1 Mutants, and Chimeras Derived from CYP102A1 Mutant It was examined whether the wild-type CYP102A1, the CYP102A1 mutants, and the chimeras derived from the CYP1.02A1 mutants may oxidize atorvastatin. Typical steady-state reactions was performed by adding 50 pmol CYP102A1 and 80 μM substrate to 0.25 ml of 100 mM potassium phosphate buffer solution (pH 7.4). In order to initiate reactions, the NADPH-generating system was added thereto (final concentrations: 10 mM glucose 6-phosphate, 0.5 mM $NADP^+$, and 1 IU yeast glucose 6-phosphate per ml). A stock solution of atorvastatin (20 mM) was prepared in DMSO and diluted into the enzyme reaction solution to have a final organic solvent concentration of <1% (v/v).

In order to measure human CYP3A4 activity, 50 pmol P450, 100 pmol NADPH-P450 reductase (CPR), 100 pmol cytochrome b5, and 45 μM L-α-dilauroyl-sn-glycero-3-phosphocholine (DLPC) were used instead of 50 pmol CYP102A1. After the reaction solution was reacted for 30 minutes at 37° C., the reaction was terminated with 2-fold of ice-cold dichloromethane.

(1) HPLC Analysis

After centrifugation of the reaction mixture, a supernatant was removed and a solvent was evaporated under nitrogen gas and analyzed using HPLC. A sample (30 ul) was injected into Gemini C18 column (4.6 mm×150 mm, 5 um. Phenomenex. Torrance, Calif.). As a mobile phase A, water containing 0.1% formic acid/acetonitrile (80/20, v/v) was used, and as a mobile phase B, acetonitrile/0.1% formic acid (90/10, v/v) was used. The mobile phase A/B (70/30, v/v) was flowed at a rate of 1 ml·$min^{-1}$ using a gradient pump (LC-20AD, Shimadzu, Kyoto, Japan). Elution solutions were detected by UV at 260 nm.

In order to examine whether or not CYP102A1 (P450 BM3) may oxidize atorvastatin, the abilities of the wild-type CYP102A1 (P450 BM3), the mutants thereof, and the chimeras derived from the CYP102A1 mutants to oxidize atorvastatin were measured at a fixed substrate concentration (80 μM).

The metabolites of atorvastatin prepared by the human CYP3A4, the bacterial CYP102A1 mutant (#16 in Table 2), and the chimera (#16A1V3) derived from the CYP102A1 were examined using HPLC chromatograms (measuring UV absorbance at 260 nm).

Peaks were confirmed by comparing with retention times of peaks of the metabolites prepared by human CYP3A4 and CYP2C9. The substrate and two main metabolites, that is, 2-hydroxylated product and 4-hydroxylated product were shown.

Figure 9:
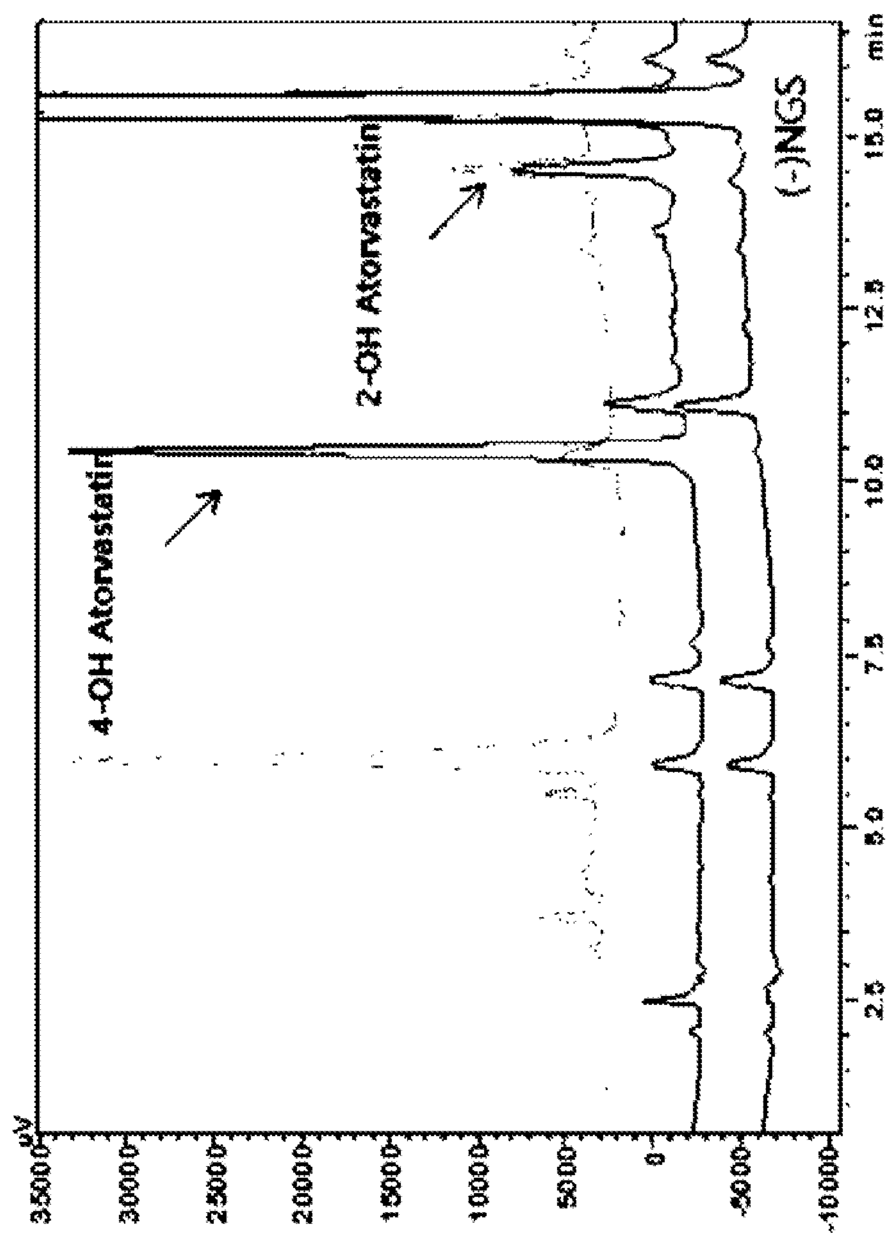
FIG. 9 shows high-performance liquid chromatography (HPLC) chromatograms (measuring UV absorbance at 260 nm) of atorvastatin metabolites produced by human CYP3A4.

As a result, it might be appreciated that retention times of the peaks of the metabolites exactly coincide with those of the standard 4-OH atorvastatin and 2-OH atorvastatin as shown in FIGS. 9 to 10B.

(2) LC-MS Analysis

In order to identify atorvastatin metabolites produced the wild-type CYP102A1 mutants and the chimeras derived from by CYP102A1 mutants, LC-MS analysis was conducted by comparing LC profiles and fragmentation patterns of atorvastatin and metabolites thereof.

The wild-type CYP102A1 mutants and human CYP3A4 were incubated with 80 μM of atorvastatin at 37° C. for 30 minutes in the presence of an NADPH-generating system. Reactions were terminated by the addition of 2-fold ice-cold $CH_2Cl_2$. After centrifugation of the reaction mixture, a supernatant was removed and an organic solvent layer was evaporated under nitrogen. The reactant was reconstituted into 100 μl of a mobile phase by vortex mixing and sonication for 20 sec. An aliquot (10 μl) of the prepared solution was injected into the LC column.

LC-MS analysis was carried out on Shimadzu LCMS-2010 EV system (Shimadzu Corporation, Japan) having LCMS solution software by electro spray ionization in a positive mode. In a Shim-pack VP-ODS column (250 mm×2.0 mm i.d., Shimadzu Corporation, Japan) water containing 0.1% formic acid/acetonitrile (80/20, v/v) was used as a mobile phase A, and acetonitrile/0.1% formic acid (90/10, v/v) was used as a mobile phase B. The mobile phase A/B (70/30, v/v) was separated using a gradient pump (LC-20AD, Shimadzu. Kyoto, Japan) at a flow rate of 0.16 ml/min. In order to identify the metabolites, mass spectra were recorded by electro spray ionization in a negative mode. Interface and detector voltages are 4.4 kV and 1.5 kV, respectively. Nebulization gas flow was set at 1.5 ml/min. and interface, curve desolvation line (CDL), and heat block temperatures were 250, 230, and 200° C., respectively.

Figure 11:
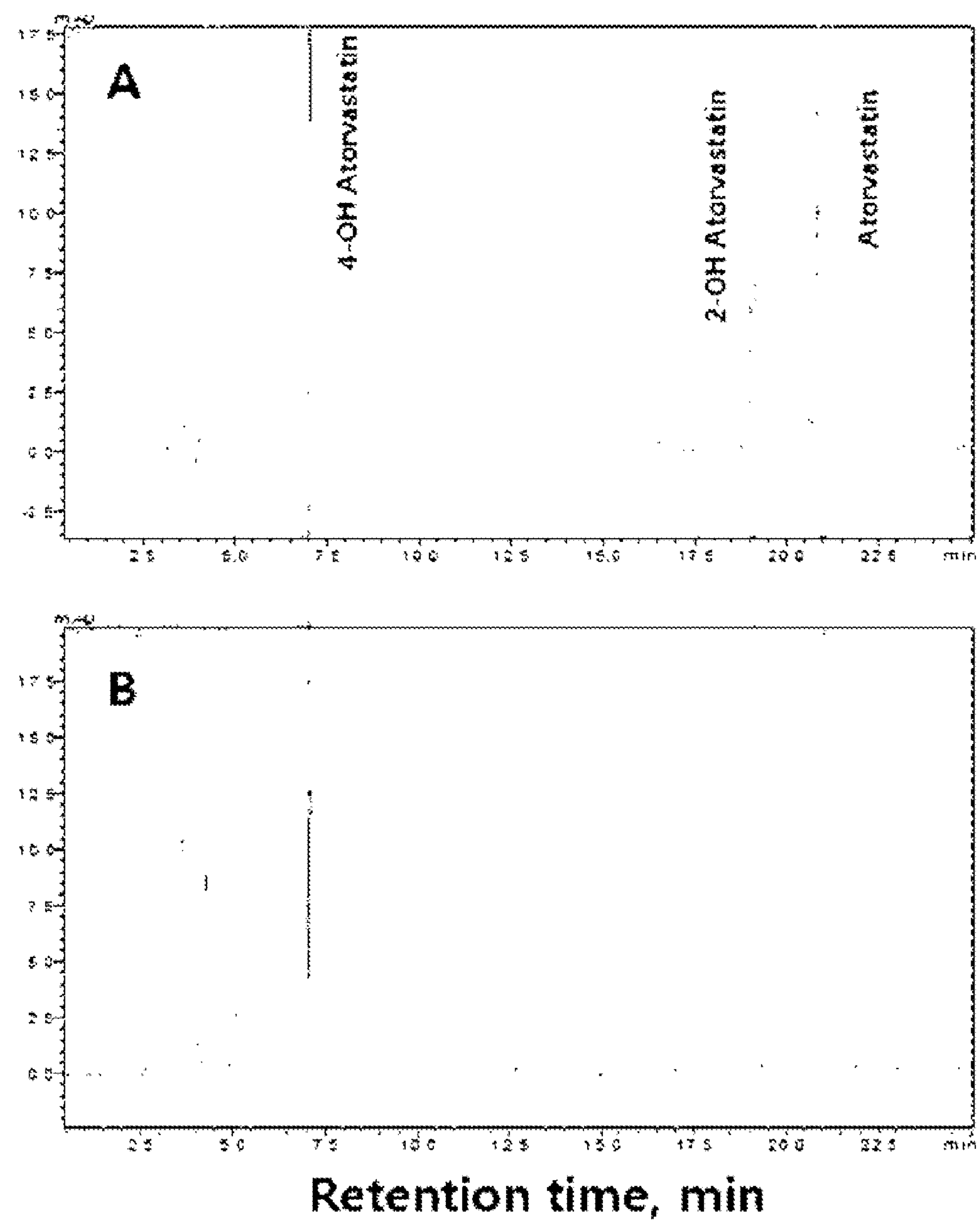
FIGS. 11A and 11B show LC-MS elution profiles of atorvastatin and metabolites thereof produced by the human CYP3A4 (FIG. 11A) and the chimera #16A1V2 derived from the CYP102A1 mutant according to the exemplary embodiment of the present invention (FIG. 11B)

As a result, it might be appreciated that in mass spectra of the reaction samples, peaks were observed at 7.183 min (4-OH atorvastatin), 19.583 min (2-OH atorvastatin), and 21.450 min (atorvastatin) as shown in total ion current (TIC) profiles of the metabolites prepared by the human CYP3A4 (A) and the chimera #16A1V2 (B) derived from the CYP102A1 mutant of FIG. 11.

Figure 12:
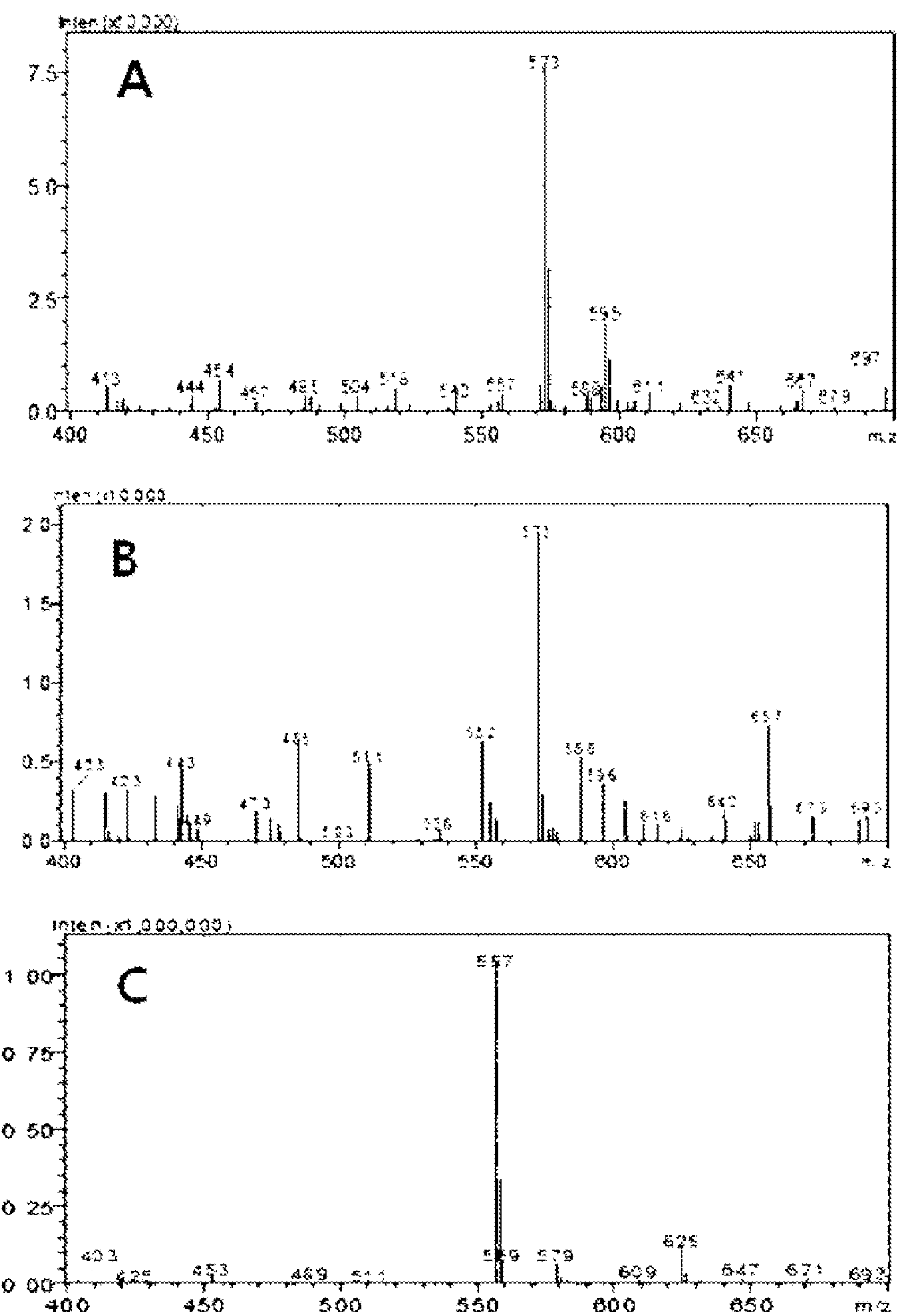
FIGS. 12A to 12C show LC-MS elution profiles of atorvastatin and metabolites thereof produced by a chimera (#16A1V2) derived from the CYP102A1 mutant according to the exemplary embodiment of the present invention.

Further, as shown in FIGS. 12A to 12C, the peaks in mass spectra of 4-hydroxylated products (A), 2-hydroxylated products (B), and atorvastatin products (C) by the chimera #16A1V2 derived from the CYP102A1 mutant were observed at 573, 573, and 557, respectively, when calculated as $[M-H]^-$.

Based on the results of LC-MS analysis of the reactants, it might be appreciated that the CYP102A1 mutants and the chimeras derived from the CYP102A1 mutants produce 4-hydroxylated or 2-hydroxylated product from atorvastatin. The retention time and fragmentation pattern of the metabolites produced by the CYP102A1 mutants and the chimeras derived from the CYP102A1 mutants were exactly matched to those of authentic metabolites produced by human CYP3A4.

(3) Determination of Turnover Number

In order to recognize production rate of atorvastatin oxides by wild-type CYP102A1, CYP102A1 mutants, and chimeras derived from the CYP102A1 mutants, the turnover number was determined in the reaction using 80 μM statin.

The term "turnover number" means the number of substrate molecules that a molecule of an enzyme may convert into products per minute and indicates conversion frequency.

The production rate of 4-hydroxylated metabolite was determined by HPLC as described above.

As shown in FIG. 13, it might be appreciated that three kinds of mutants (#15, #16, and #17 in Table 2) and five kinds of chimeras (#16A1V2, #16A1V3, #17A1V2, #17A1V3, and #17A1V8) derived from the mutants have high turnover number as the results of measuring the turnover numbers of 17 kinds of mutants and 7 kinds of chimeras derived from the mutants in oxidation of atorvastatin (producing the metabolites of atorvastatin).

Particularly, it might be appreciated that the chimeras #16A1V2 and #17A1V2 derived from the mutants have the same activity as that of the human CYP3A4.

In order to recognize production rate of atorvastatin metabolites by the CYP102A1 mutant (#16 in Table 2) and the chimeras (#16A1V2 and #17A1V2) derived from the CYP102A1 mutants, total turnover numbers (TTNs; mol product/mol catalyst) were determined in reactions using total 240 μM atorvastatin.

The term "total turnover number (TTN)" means the number of substrate molecules converted into metabolites by enzymes for the total reaction time.

The total turnover numbers (TTNs) were determined by comparing the results under three conditions. First, the reaction was performed by adding a NADPH-generating system at 37° C. for 1 hour in the presence of 80 μM substrate. In addition, second, after reaction was performed for 1 hour in the presence of 80 μM substrate, 80 μM substrate was additionally added to the reaction mixture, and the reaction was further performed for 1 hour. Finally, after reaction was performed for 1 hour in the presence of 80 μM substrate, 80 μM substrate was additionally added to the reaction mixture, and the reaction was further performed for 1 hour. Then, 80 μM substrate was additionally added to the reaction mixture, and the reaction was further performed for 2 hours.

The production rate of the atorvastatin metabolites was determined using HPLC. The enzyme capable of most efficiently producing a large amount of metabolites in vitro may be selected by comparing the results according to concentration of the substrate and reaction time using mutants or chimeras derived from the mutants having higher activity based on experimental results of the turnover number.

As a result, the total turnover numbers (TTNs; mol product/mol catalyst) were in a range of 31 to 83 as shown in FIG. 14.

Particularly, when the chimeras #16A1V2 and #17A1V2 derived from CYP102A1 mutants having high activity were reacted for 4 hours, it might be appreciated that #16A1V2 has activity higher than that of the human CYP3A4.

The production of metabolites of atorvastatin by chemical synthesis has never been reported up to now. Therefore, it may be an alternative to chemical synthesis of the target metabolites in the Examples of the present invention to use CYP102A1 enzymes, that is, CYP102A1 mutants and the chimeras derived from the CYP102A1 mutants to generate the metabolites of atorvastatin according to the present invention.

According to the present invention, it might be appreciated that bacterial CYP102A1 enzymes of the Examples catalyze the same reaction as that of the human CYP3A4 to produce 4-OH product and 2-OH product, which are the human metabolites.

In addition, it might be appreciated that the wild-type CYP102A1 mutants and the chimeras derived from the CYP102A1 mutants catalyze oxidation of atorvastatin, which is the human P450 substrate, and produces 4-hydroxylated product and 2-hydroxylated product, which are the main metabolites produced by the human CYP3A4, from atorvastatin.

Further, it may be appreciated that the wild-type CYP102A1 mutants and the chimeras derived from the CYP102A1 mutants according to the present invention may efficiently produce the human metabolites from atorvastatin, these metabolites may be used to estimate effect, toxicity, and pharmacokinetics of drugs, or the like in a process of developing the drugs, and used to prepare human metabolite derivatives capable of serving as a lead compound of developing the drug.

Sequence Listing Free Text

SEQ. ID. NO: 1 to 15 are primer sequence

SEQ. ID. NO: 16 is an amino acid sequence of a wild-type CYP102A1

SEQ. ID. NO: 17 is a nucleotide sequence of a wild-type CYP102A1

SEQ. ID. NO: 18 is an amino acid sequence of a wild-type CYP102A1 mutant #16

SEQ. ID. NO: 19 is a nucleotide sequence of a wild-type CYP102A1 mutant #16

SEQ. ID. NO: 20 is an amino acid sequence of a wild-type CYP102A1 mutant #17

SEQ. ID. NO: 21 is a nucleotide sequence of a wild-type CYP102A1 mutant #17

SEQ. ID. NO: 22 is an amino acid sequence of a chimera #16A1V2 derived from the wild-type CYP102A1 mutant #16

SEQ. ID. NO: 23 is a nucleotide sequence of a chimera #16A1V2 derived from the wild-type CYP102A1.

The invention claimed is:

1. A method for preparing a 2-hydroxylated product or a 4-hydroxylated product of atorvastatin comprising:

reacting at least one enzyme comprising a chimera derived from a CYP102A1 mutant with atorvastatin for a time period of at least two hours, wherein the CYP102A1 mutant has an amino acid sequence changed from that of the wild-type CYP102A1 by at least one substitution selected from the group consisting of R47L/E64G/F87V/E143G/L188Q/E267V, R47L/F81I/F87V/E143G/L188Q/E267V, and R47L/E64G/F81I/F87V/E143G/L188Q/E267V and wherein the chimera from the CYP102A1 mutant includes an amino acid substitution position and substituted amino acid in the CYP102A1 mutant selected from the group consisting of A475V/E559D/T665A/P676L/A679E/E688A/A742G/K814E/R826S/R837H/E871N/1882V/E88 8G/P895S/S955N/M968V/Q982R/A1009D/H1022Y/Q1023E, A475V/E559D/T665A/A679E/E688A/A742G/K814E/E871N/1882V/E888G/P895S/G913G/S95 5N/M968V/A1009D/H1022Y/Q1023E, and K474T/A475V/Q547E/D600EN625L/D638E/K640A/G661R/T665A/Q675K/T716A/A717T/A7 42G/A783V/K814E/1825M/E871N/1882V/E888G/D894G/E948K/S955N/M968V/A1009D/D10 20E; and wherein total turnover number of atorvastatin is increased as compared to same reaction in which the CYP102A1 mutant is reacted with atorvastatin.

2. The method of claim 1, further comprising adding a NADPH-generating system.

3. The method of claim 2, wherein the NADPH-generating system includes glucose 6-phosphate, NADP+, and yeast glucose 6-phosphate dehydrogenase.

* * * * *